(12) United States Patent
Weinstein et al.

(10) Patent No.: US 8,037,884 B2
(45) Date of Patent: Oct. 18, 2011

(54) MODULAR SYSTEM FOR PATIENT POSITIONING DURING MEDICAL PROCEDURES

(75) Inventors: Samantha A. Weinstein, Waltham, MA (US); Thomas K. Skripps, Acton, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 891 days.

(21) Appl. No.: 11/865,337

(22) Filed: Oct. 1, 2007

(65) Prior Publication Data

US 2008/0078031 A1 Apr. 3, 2008

Related U.S. Application Data

(60) Provisional application No. 60/848,501, filed on Oct. 2, 2006, provisional application No. 60/863,522, filed on Oct. 30, 2006.

(51) Int. Cl.
*A61G 15/00* (2006.01)

(52) U.S. Cl. ............... 128/845; 602/16; 602/32

(58) Field of Classification Search ............. 602/32–36; 128/845; 248/118, 116; 5/624, 646, 658
See application file for complete search history.

(56) References Cited

U.S. PATENT DOCUMENTS

| | | |
|---|---|---|
| 2,586,417 A | 2/1952 | Cole |
| 3,188,079 A | 6/1965 | Boetcker et al. |
| 3,528,413 A | 9/1970 | Aydt |
| 3,572,835 A | 3/1971 | Kees, Jr. |
| 3,761,128 A | 9/1973 | Schenk et al. |
| 4,108,426 A | 8/1978 | Lindstroem et al. |
| 4,159,093 A | 6/1979 | Hamilton |
| 4,702,465 A | 10/1987 | McConnell |
| 4,717,133 A | 1/1988 | Walsh et al. |
| 6,199,812 B1 | 3/2001 | Schuepbach |
| 6,663,055 B2* | 12/2003 | Boucher et al. ............... 248/118 |
| 7,234,180 B2 | 6/2007 | Horton et al. |
| 2001/0039680 A1 | 11/2001 | Boucher et al. |
| 2002/0170115 A1 | 11/2002 | Borders et al. |
| 2006/0242765 A1 | 11/2006 | Skripps et al. |
| 2006/0248650 A1 | 11/2006 | Skripps |
| 2006/0253985 A1 | 11/2006 | Skripps |
| 2006/0255220 A1 | 11/2006 | Skripps |

FOREIGN PATENT DOCUMENTS

| | | |
|---|---|---|
| WO | 0193796 A | 12/2001 |
| WO | 2005037165 A | 4/2005 |

OTHER PUBLICATIONS

Mayfield Horseshoe and Skull Tongs Adaptation Instruction Manual. Orthopedic Systems, Inc. 1992.
Mayfield Surgical Devices. Base Units and Adaptors. Integra LifeSciences Corporation. 2005.
European Partial Search Report "Patent Application EP 07253906," The Hague (Place of Search), (Apr. 7, 2009).

* cited by examiner

*Primary Examiner* — Michael A. Brown
(74) *Attorney, Agent, or Firm* — Barnes & Thornburg LLP

(57) ABSTRACT

A device 50 for supporting and positioning a part of a patient's body includes at least two joints 62, 64, 66 each having a locked state and an unlocked state and a release system for allowing an operator to select between the locked state and the unlocked state. The release system has an operator interface remote from the joints and at a location that enables the operator to support the weight of the body part while at least one of the joints is in the unlocked state.

44 Claims, 22 Drawing Sheets

MODULAR SYSTEM FOR PATIENT POSITIONING DURING MEDICAL PROCEDURES

CROSS REFERENCE TO RELATED APPLICATIONS

This application claims priority to U.S. Provisional Patent Application No. 60/848,501 entitled "MODULAR SYSTEM FOR POSITIONING OF HEAD DURING SURGICAL PROCEDURES" filed on Oct. 2, 2006 and U.S. Provisional Application No. 60/863,522 entitled "MODULAR SYSTEM FOR POSITIONING OF HEAD DURING SURGICAL PROCEDURES" filed on Oct. 30, 2006, the contents of both of which are expressly incorporated by reference herein.

BACKGROUND OF THE INVENTION

This application describes an apparatus for supporting and positioning a body part of a patient during medical procedures, and more particularly describes a device developed in the context of supporting and positioning the patient's head during surgery of the spine.

During preparation for surgery, and during the surgery itself, it is necessary for the surgical team to support and position the patient's head in a way that allows appropriate access to the surgical site. Typical pre-existing positioning devices have multiple adjustments that require several members of the surgical team to participate in head positioning— one member to operate one or more of the adjustments and one member to support the patient's head during adjustment. This can be a time consuming and tedious way to achieve satisfactory positioning. Moreover, some devices allow adjustability in only discrete increments, rather than offering a continuous spectrum of adjustability. The discrete adjustability can result in suboptimal positioning.

Accordingly, it is desirable to provide a device for support and positioning that can be adjusted by a single person and that provides a wide range of continuous adjustability. It is also desirable to provide a device that can accept a number of different head engagement modules, each of which can be easily attached to or disengaged from the positioning device. It is also desirable to enable the person operating the device to support the weight of the patient's head during position adjustment.

SUMMARY

A device for supporting and positioning a part of a patient's body comprises at least two joints each of which has a locked state and an unlocked state and a release system for allowing an operator to select between the locked state and the unlocked state. The release system has an operator interface remote from the joints and at a location that enables the operator to support the weight of the body part while at least one of the joints is in the unlocked state.

A coupling for securing an accessory to a host component comprises a housing associated with either of the accessory and the host component. The housing has a cavity and a pair of jaw halves each radially deployable into and out of the cavity. An attachment feature associated with the other of the accessory and the host component has a pair of opposing capture slots. When the attachment feature is mated with the housing, the attachment feature nests radially inside the housing cavity with each jaw half residing in one of the capture slots.

A mirror assembly comprises a primary mirror, a secondary mirror hinged to the primary mirror, a lamp on the non-reflective side of the primary mirror and a light refractor on the reflective side of the primary mirror.

An adaptor for adapting an accessory for securement to a host component when the host component has a receptor and the accessory has an attachment element not compatible with the receptor. The adaptor has an attachment end with a receiver compatible with the accessory attachment element and a host component end having an attachment feature compatible with the receptor.

DETAILED DESCRIPTION

Figure 1:
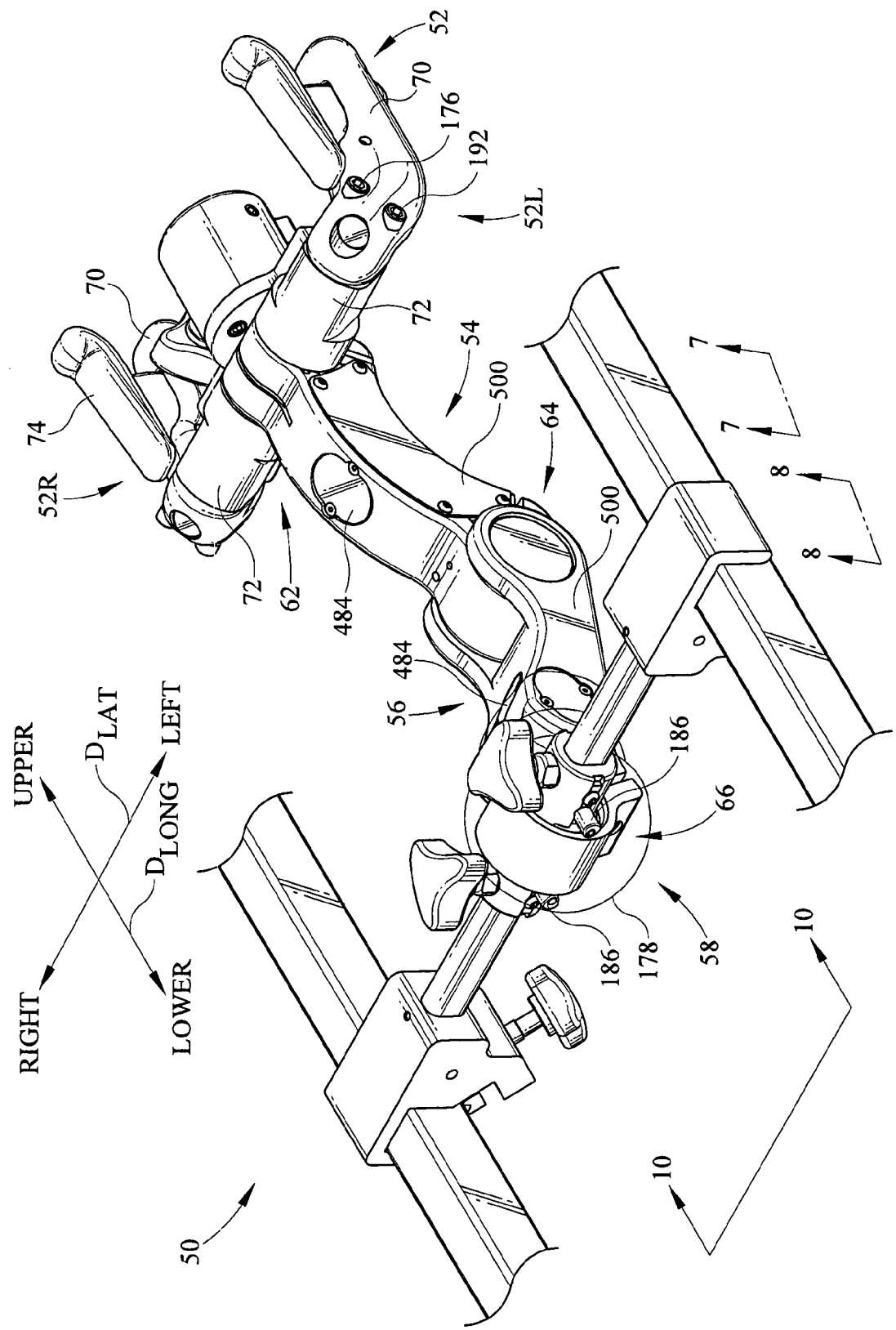
FIG. 1 is a perspective view of a support and positioning device as disclosed herein.

Referring to FIG. 1, a device 50 for supporting and positioning a patient's head during surgery includes a handle assembly 52, an upper arm 54 extending longitudinally from the handle assembly, and a lower arm 56 extending longitudinally from the upper arm to a mount 58. A wrist joint 62 defines an interface between the handle assembly and the upper arm. An elbow joint 64 defines an interface between the upper arm and the lower arm. A shoulder joint 66 defines an interface between the lower arm and the mount 58. As described in more detail hereinafter, each joint has a locked state and an unlocked state. The device itself has a rest state corresponding to the locked state of all the joints and an active state corresponding to an unlocked state of at least one of the joints.

As used herein, and as indicated in FIG. 1, "longitudinal" refers to a direction $D_{LONG}$ along the length of the arms, and "lateral" refers to a side-to-side direction $D_{LAT}$. "Upper" and "lower" are relative terms referring to locations longitudinally closer to the wrist joint and the shoulder joint respectively. Thus, the elbow joint 64 is in a upper position relative to the shoulder joint 66, but in a lower position relative to the wrist joint 62. "Up" and "down" are counterparts to "upper" and "lower". The terms "right" and "left" are directional terms used from the perspective of a patient lying face down relative to the device (See FIG. 14) "Top" and "bottom" refer to views of the device as seen by an observer looking at the device from above or from underneath respectively when the device is properly mounted on rails of an operating table. Axial, radial and circumferential designations are also employed as necessary to describe local directions in relation to local features or components.

Figure 2:
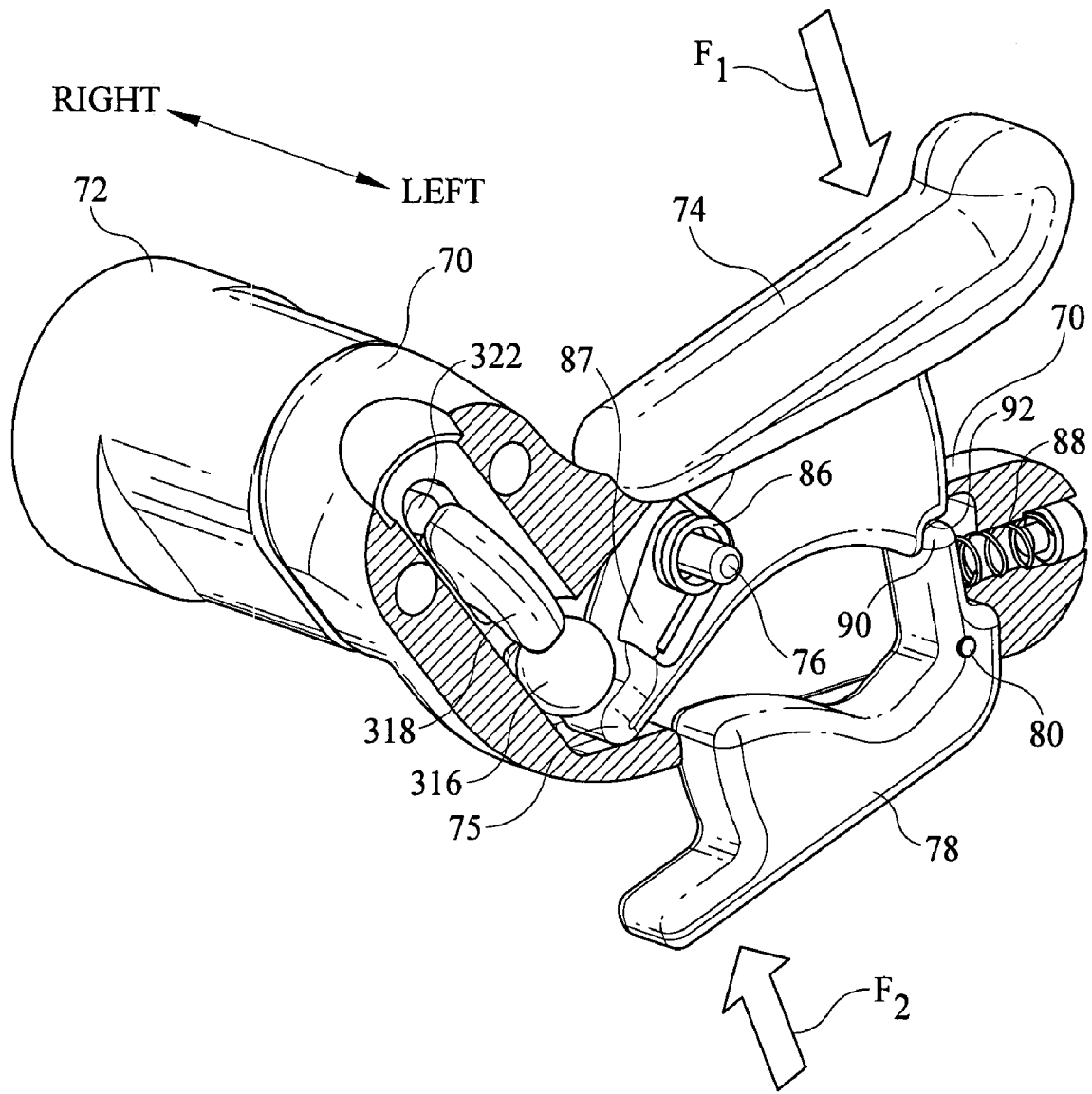
FIG. 2 is a partially broken away, perspective view of a handle assembly for the device of FIG. 1.
Figure 3A:
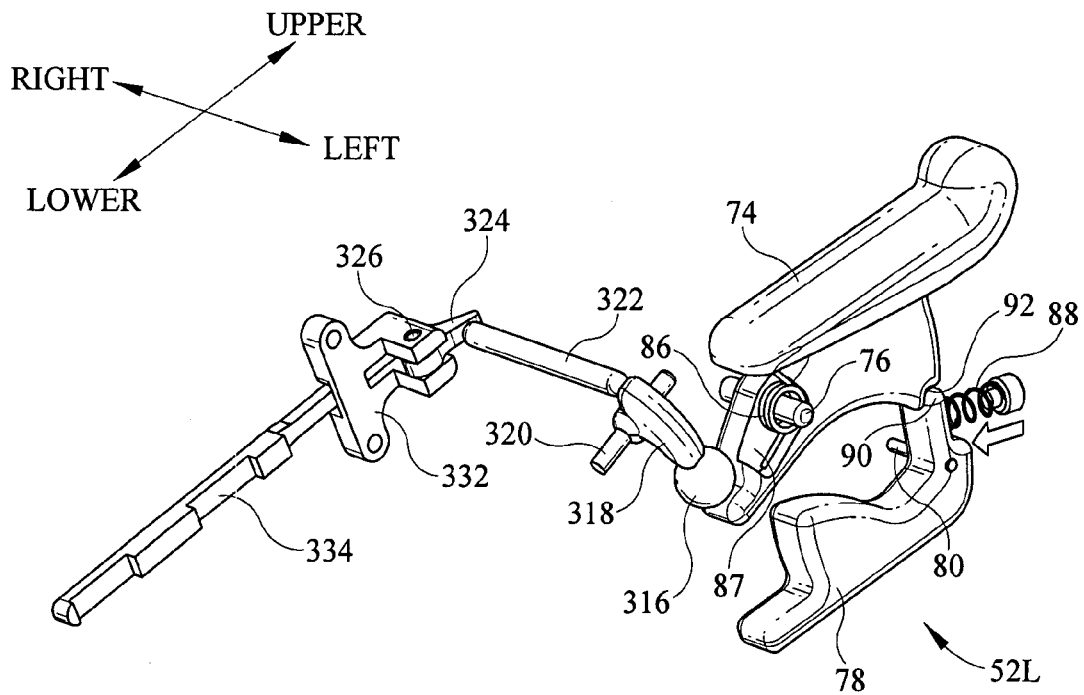
FIGS. 3A and 3B are views similar to FIG. 2 showing components of a handle assembly in an unreleased state and a released state respectively and also showing selected elements of a motion transfer system.
Figure 3B:
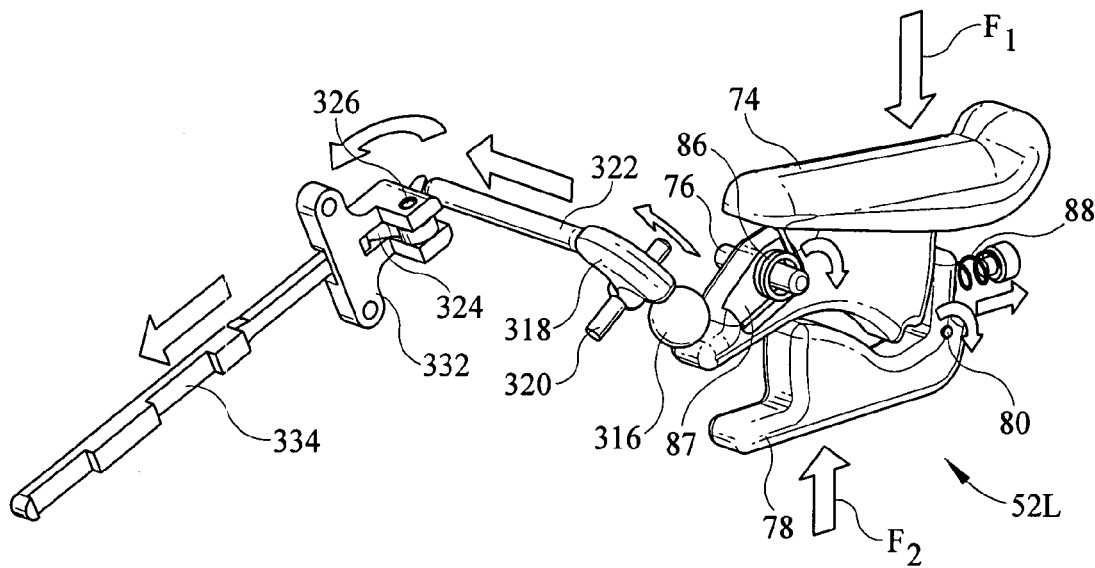
Figures 9A, 9B:
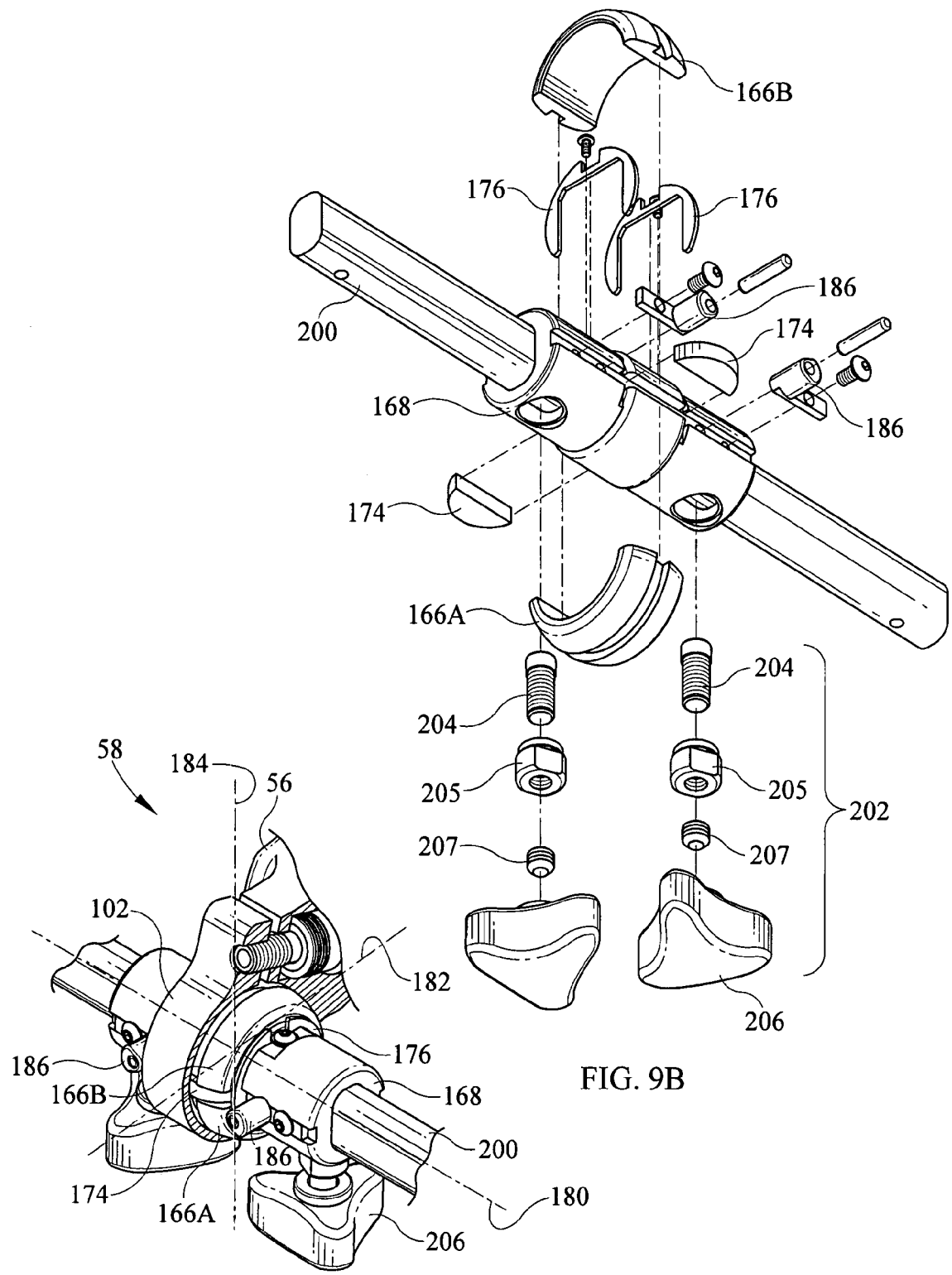
FIGS. 9A and 9B are an assembled view and an exploded view showing components of a mount, one side of a shoulder ring being cut away in FIG. 9A to expose a pair of ball pivot halves.
Figure 10A:
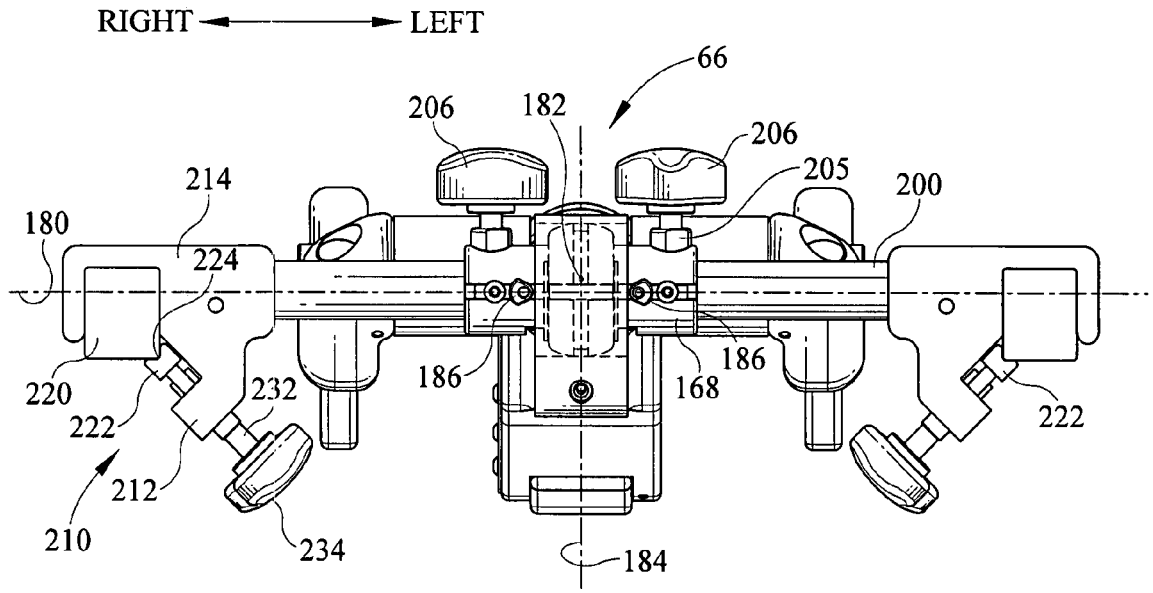
FIGS. 10A and 10B are views of the mount taken substantially in the direction 10-10 of FIG. 1. showing the shoulder joint in a baseline orientation and rotated about a roll axis.
Figure 10B:
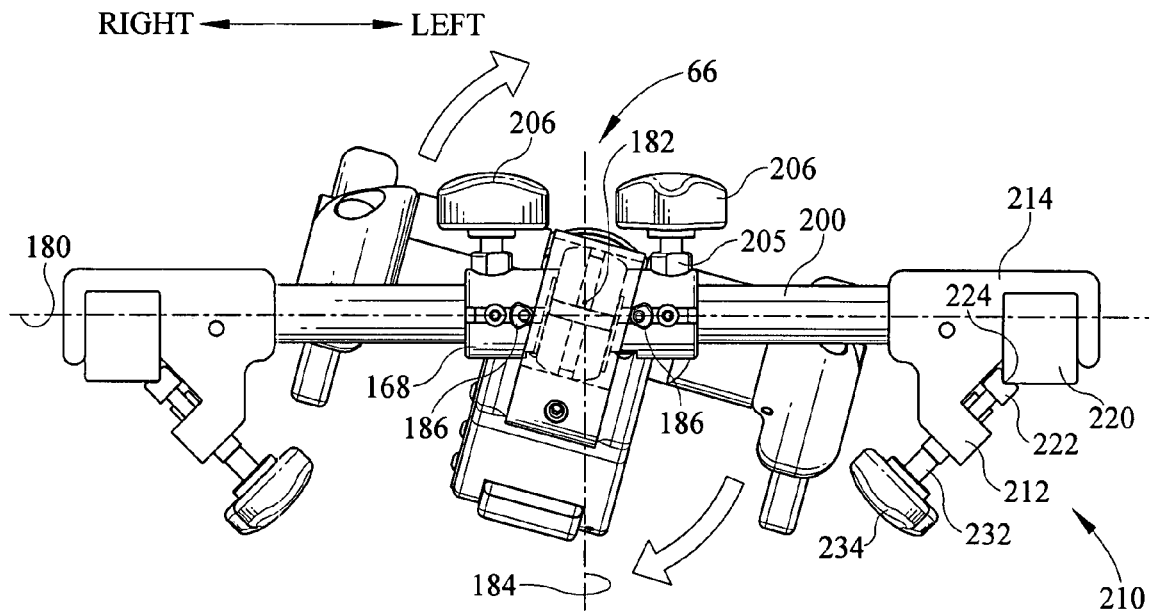

Referring additionally to FIGS. 2, 3A and 3B, the handle assembly 52 comprises left and right handle assemblies 52L, 52R. The handle assemblies are substantially similar to each other and it will suffice to describe only the left handle assembly in detail. The left handle assembly comprises a handlebar 70, an operator interface, and a handle half 72 connected to the handlebar. The operator interface includes a handle lever 74 connected to the handlebar by pivot 76, and an interlock 78 connected to the handlebar by pivot 80. A torsion spring 86 nests in a recess 87 in the handle lever and engages the handle lever and the handlebar to urge the handle lever counterclockwise about its pivot (as seen from the perspective of FIG. 9). A coil spring 88 engages the interlock and the handlebar to urge the interlock counterclockwise about its pivot. With the handle lever and interlock so urged, a projection 90 extending from the interlock engages a smoothly curved notch 92 on the handle lever (FIGS. 2, 3A). As a result, the handle lever will not rotate about pivot 76 in response to an operator force $F_1$ applied to the handle lever. However an additional operator force $F_2$ applied concurrently to the interlock will disengage the projection 90 from the notch 92, thereby permitting rotation of the handle lever as seen in FIG. 3B. Removal of the operator forces $F_1$, $F_2$ allows the spring 88 to return the interlock to the position shown in FIGS. 2A and 3 and allows the spring 86 to assist in returning the handle lever its interlocked position seen in FIGS. 2A and 3.

As seen most clearly in FIGS. 4A, 4B, 5A and 5B, the upper arm 54 includes a wrist ring 98 at its upper end and a larger diameter elbow ring 100 at its lower end. The lower arm 56 includes a shoulder ring 102 at its lower end and a yoke 104 at its upper end. A large hole 106 penetrates one flank of the yoke. A small hole 108 (partially visible in FIG. 8) penetrates the other flank of the yoke.

The wrist ring 98 is an axially split ring having a proximal flange 110, a distal flange 112 and a bore 113. A proximal, unthreaded bolt hole 114 penetrates through the proximal flange; a distal, threaded bolt hole 116 resides in the distal flange. The ring 98 is elastically deformable such that its flanges can be displaced circumferentially toward or away from each other.

Figure 6A:
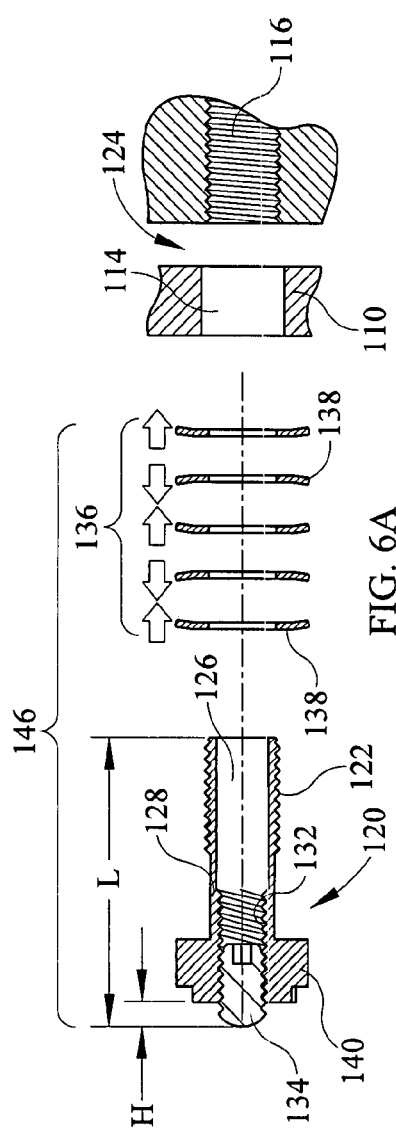
FIGS. 6A through 6C are schematic, cross sectional side elevation views each showing a bolt and washer array associated with the wrist, elbow and shoulder joints respectively.

Referring additionally to FIG. 6A, a bolt 120 passes through the proximal hole 114, which is radially oversized relative to the bolt shank 122, spans across interflange gap 124 and threads into the distal hole 116. The bolt is a hollow shank bolt having a full length bore 126 with an internal shoulder 128 and internal threads 132 in the vicinity of bolt head 140. An oval "point" set screw 134 is threaded into the bolt bore and allows the effective length L of the bolt to be adjusted. An array 136 of spring washers 138 resides between the bolt head 140 and the proximal flange 110.

Figure 4A:
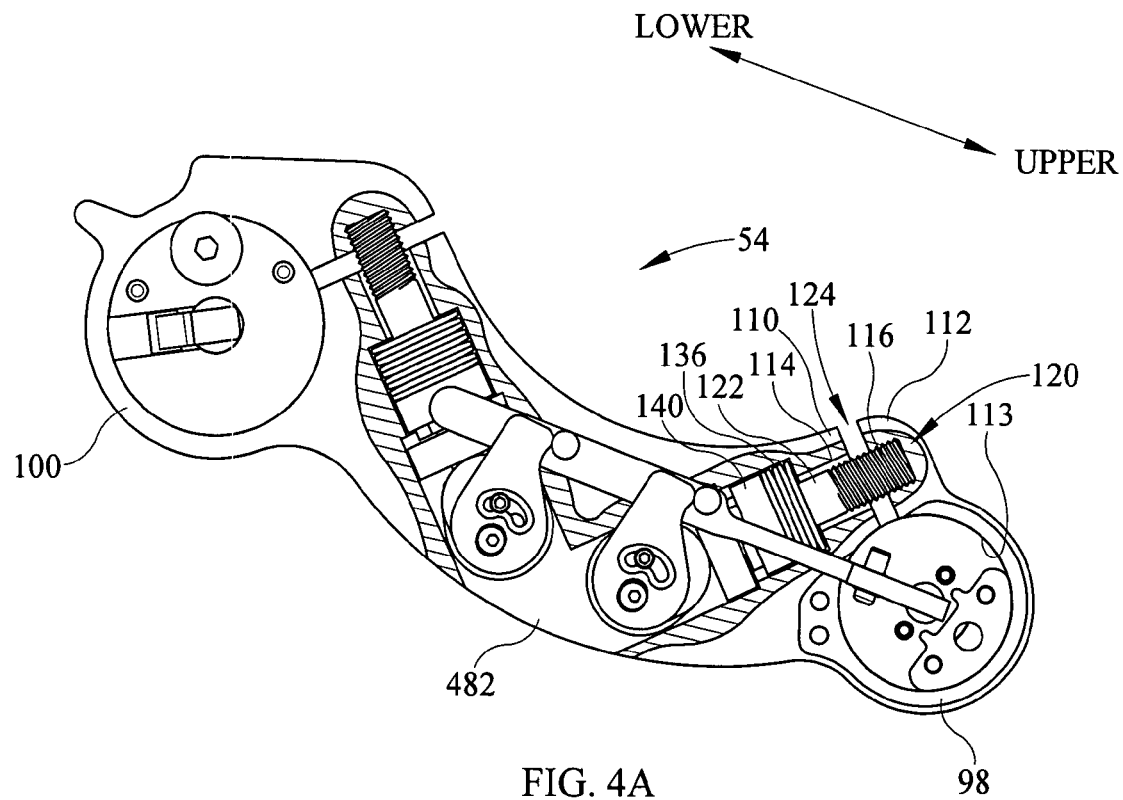
FIGS. 4A and 4B are cross sectional right side elevation views of an upper arm of the device of FIG. 1 showing wrist and elbow joints in locked and unlocked states respectively.
Figure 4B:
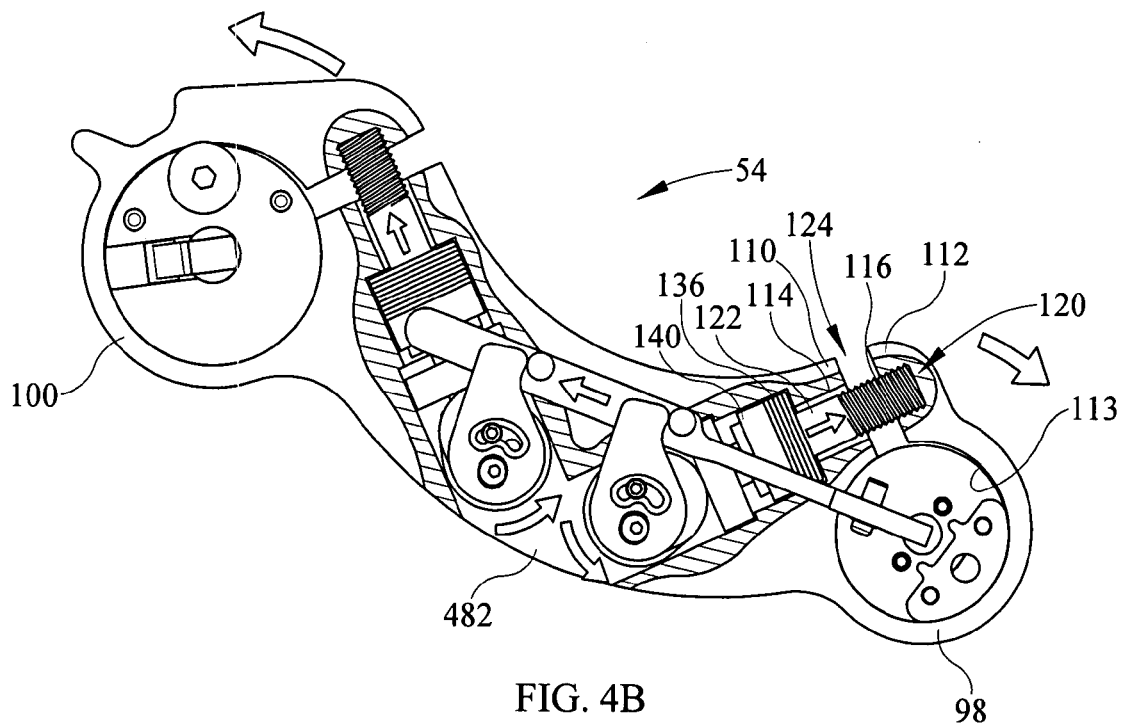
Figure 5A:
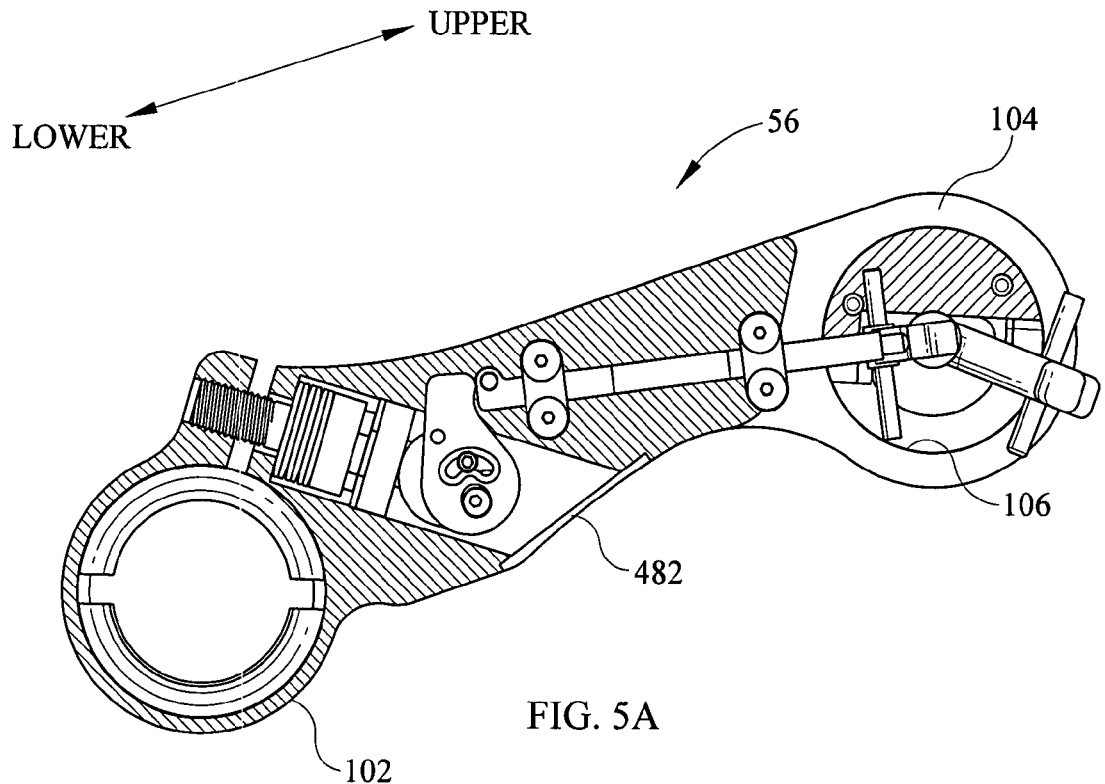
FIGS. 5A and 5B are cross sectional right side elevation views of a lower arm of the device of FIG. 1 showing a shoulder joint in locked and unlocked states respectively.
Figure 5B:
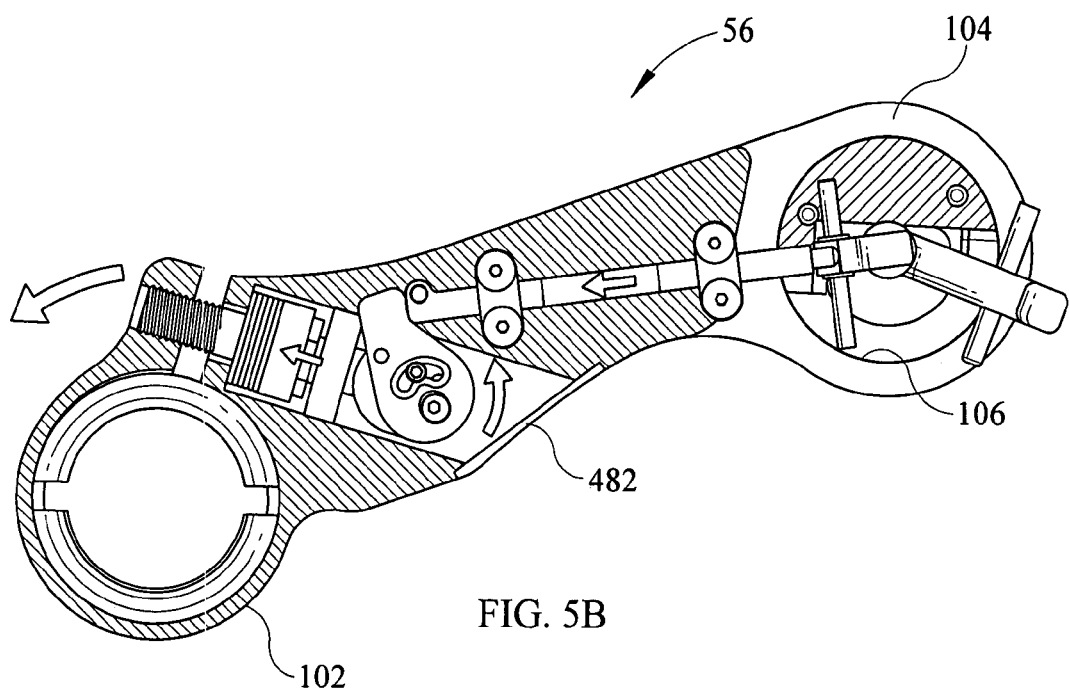

The deformable wrist ring 98, in concert with the bolt and washer array 136 serves as a lock for the wrist joint 62. The bolt and washers serve as an actuation member 146 for locking and unlocking the lock, i.e. for locking and unlocking the joint. The wrist joint, like the elbow and shoulder joints, is normally in a locked state, i.e. gap 124 is small as seen in FIG. 4A so that the ring 98 grips a joint component residing in the bore 113 of the ring. As described in more detail below, operation of the operator interface spreads the distal flange 112 away from the proximal flange 110, thus unlocking the joint as seen in FIG. 4B. During assembly of the device, the set screw 134 can be accessed with an allen wrench inserted into the shank end of the bore 126. The height H of the set screw relative to the bolt head can then be adjusted to govern the effective length L of the bolt thereby regulating the gripping force at the wrist joint.

Figure 6B:
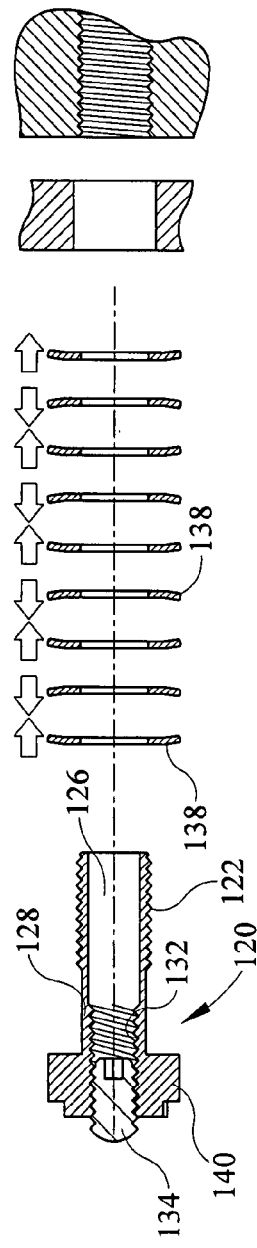
Figure 6C:
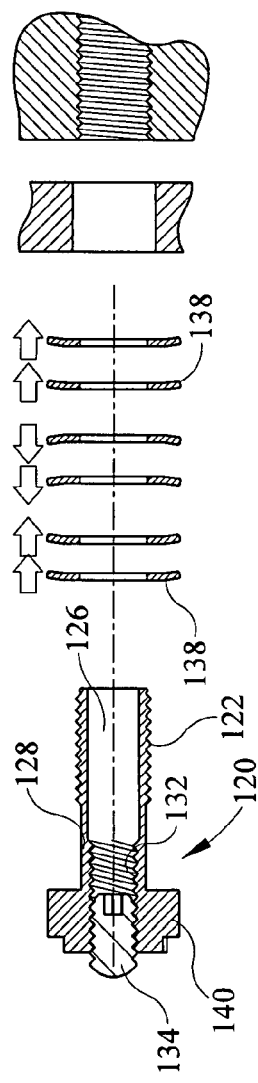

The elbow and shoulder rings are similar to the wrist ring except for their physical dimensions. For example, in the illustrated device both the elbow and shoulder rings are equal in diameter to each other but are of larger diameter than the wrist ring. The elbow and shoulder locks formed by the elbow and shoulder rings are similar to the wrist lock except for the quantity and orientations of the individual washers that make up the washer array. The washer arrays for the wrist, elbow and shoulder joints for the illustrated embodiment of the device 50 are seen in FIGS. 6A, 6B and 6C respectively.

As described above, the upper arm 54 includes a wrist ring 98 circumscribing the wrist joint and an elbow ring 100 circumscribing the elbow joint. The lower arm 56 includes a shoulder ring 102 circumscribing the shoulder joint and a yoke 104. However the yoke could instead be present on the upper arm and the elbow ring on the lower arm. Appropriate changes in the specific layout of a motion transfer system, which is described below, would be required to accommodate the presence of the yoke on the upper arm and the elbow ring on the lower arm. In principle, either arm, but not both, may include the elbow ring.

Figure 7:
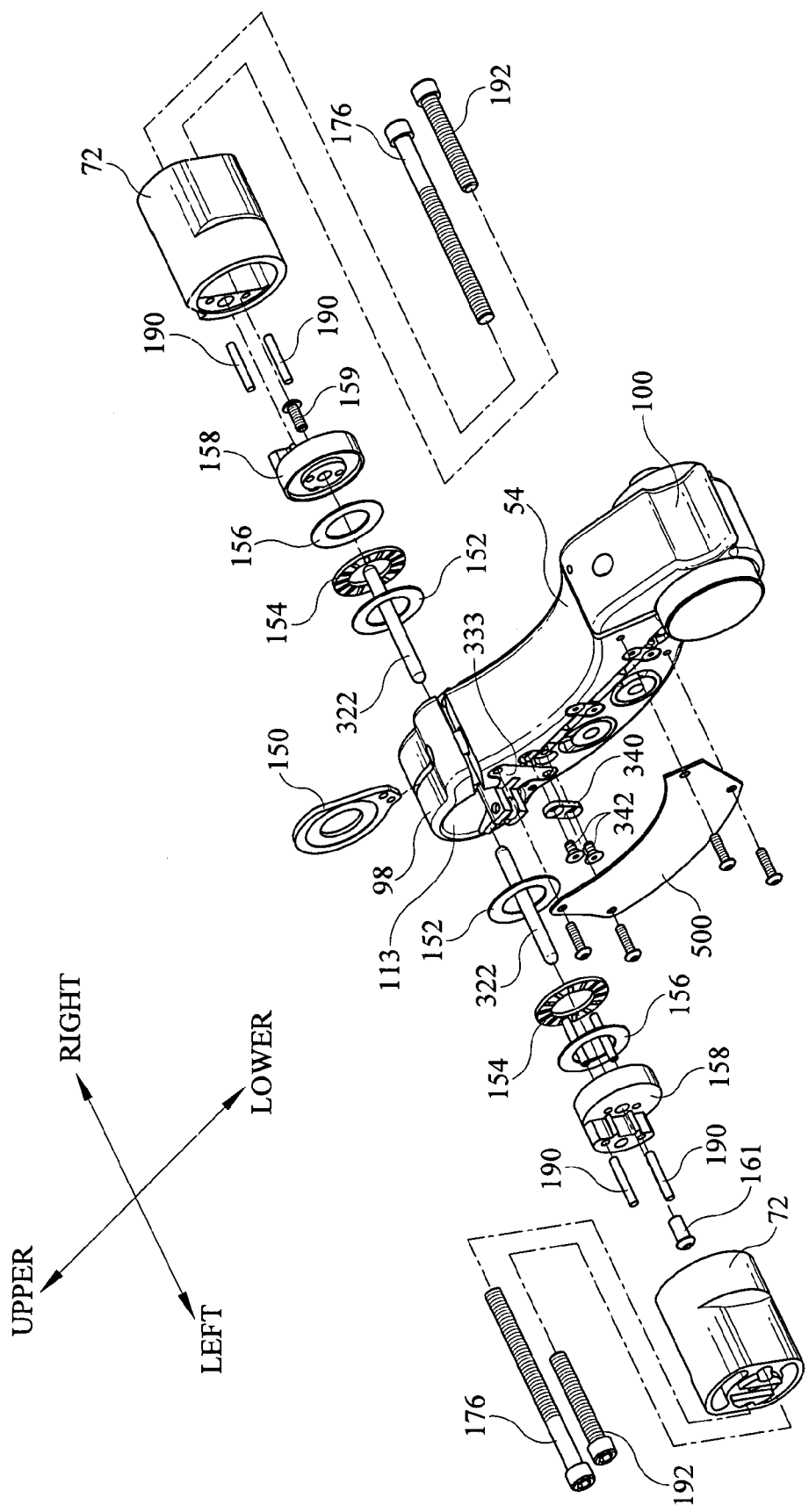
FIG. 7 is an exploded view taken substantially in the direction 7-7 of FIG. 1 showing the upper arm, components of the wrist joint and selected components of the handle assembly.

FIG. 7 is an exploded view taken substantially in the direction 7-7 of FIG. 1 showing a bottom view of the upper arm, components of the wrist joint, and selected components of the handle assembly. The wrist ring 98 of the upper arm 54 circumscribes components of the wrist joint so that those wrist joint components reside in bore 113 of the wrist ring. These components include a center disk 150, an axially inner pair of thrust washers 152 bordering the center disk, a pair of thrust bearings 154 bordering the inner pair of thrust washers, an axially outer pair of thrust washers 156 bordering the thrust bearings and a pair of center halves 158 bordering the axially outer thrust washers. A screw 159 and a barrel nut 161 hold the above described components together. When the wrist joint is locked, the wrist ring grips the center halves so that the center halves and wrist ring are rotationally fixed relative to each other. When the wrist joint is unlocked, relative rotation of the center halves and wrist ring about the axis of bore 113 is enabled. Specifically, the wrist ring is rotatable about the center halves.

Figure 8:
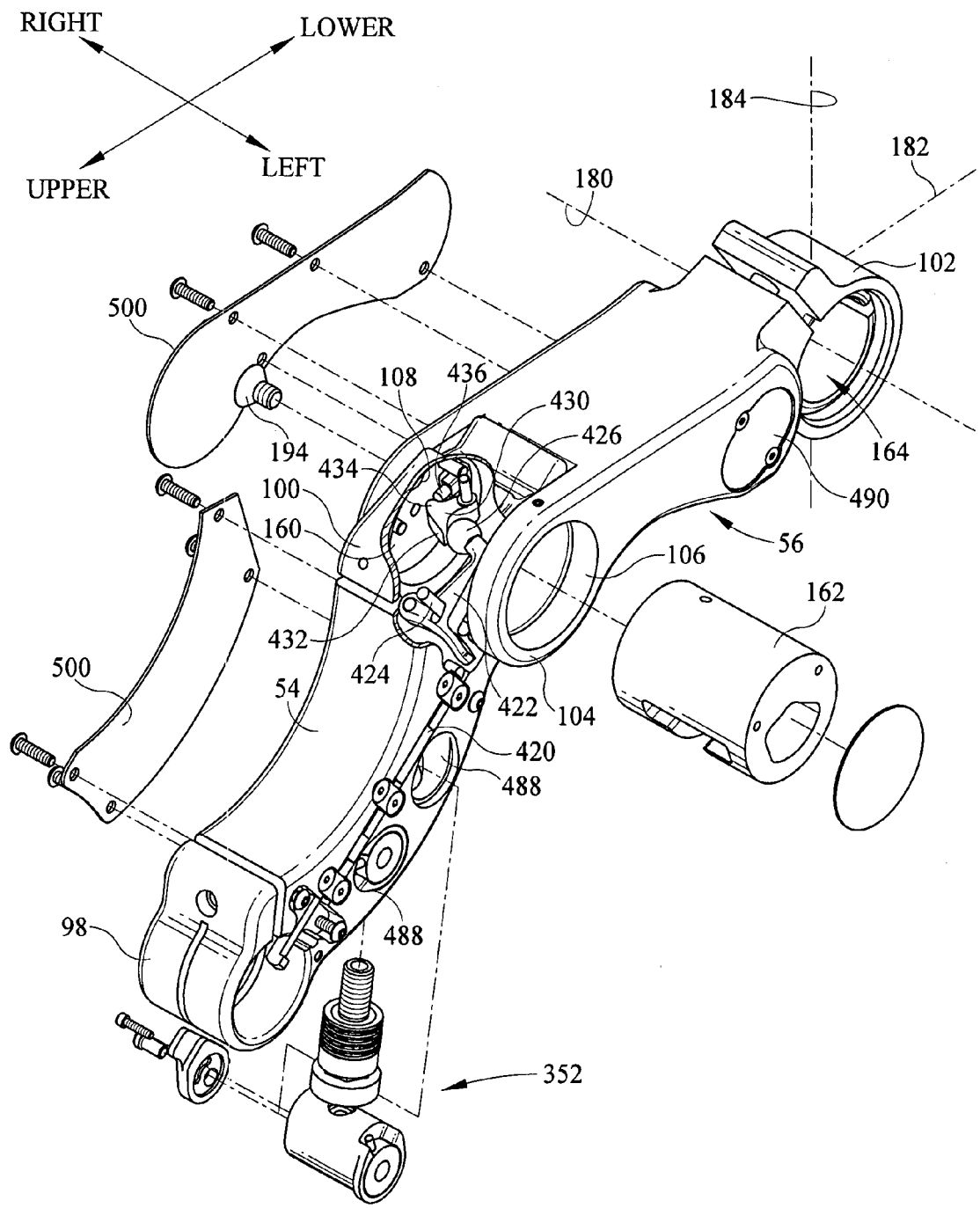
FIG. 8 is an exploded view taken substantially in the direction 8-8 of FIG. 1 showing the upper and lower arms, components of a shoulder joint, and an elbow cam assembly.

FIG. 8 is an exploded view taken substantially in the direction 8-8 of FIG. 1 showing a bottom view of the upper and lower arms, components of a shoulder joint, and an elbow cam assembly. The elbow ring 100 of the upper arm 54 circumscribes components of the elbow joint so that those elbow joint components reside in the bore 160 of the elbow ring. These components include an arm pivot 162. When the elbow joint is locked, the elbow ring grips the arm pivot so that the arm pivot and elbow ring are rotationally fixed relative to each other. When the elbow joint is unlocked, relative rotation of the arm pivot and elbow ring about the axis of bore 160 is enabled. Specifically the elbow ring is rotatable about the arm pivot.

Referring additionally to FIGS. 9A, 9B, 10A and 10B, the shoulder ring 102 circumscribes components of the shoulder joint. These components include a pivot assembly which includes a ball pivot 166 (comprising ball pivot halves 166A, 166B) and a ball pivot sliding shaft 168 secured to the ball pivot halves with a pair of keys 174. The keys prevent the ball pivot halves from moving radially inwardly toward axis 180 of the bore 164 of the shoulder ring. A pair of retainers 176 laterally secures the ball pivot sliding shaft 168 relative to the shoulder ring with the shaft 168 projecting laterally beyond the lateral extremities of the shoulder ring. A resilient boot 178, illustrated in phantom in FIGS. 1 and 14-17, covers the joint. When the shoulder joint is locked, the shoulder ring grips the pivot assembly so that the pivot assembly and the shoulder ring are rotationally fixed relative to each other. Specifically, the shoulder ring grips the ball pivot halves. When the shoulder joint is unlocked, relative rotation of the ball pivot assembly and shoulder ring about the axis of bore 164 is enabled. Specifically, the shoulder ring is rotatable about the ball pivot assembly. The substantially spherical geometry of the ball pivot 166 causes the joint to be pivotable not only about the shoulder bore axis 180, but also about a roll axis 182. In principle, the shoulder ring is also rotatable about a yaw axis 184. However the illustrated embodiment includes a pair of swing stops 186 secured to the ball pivot sliding shaft. The swing stops contact the shoulder ring 102 to substantially prevent rotation about the yaw axis.

As seen from the foregoing, the wrist and shoulder joints are each pivotable about only a single axis, whereas the shoulder joint is pivotable about two axes and, but for the swing stops 186, would be pivotable about three orothogonal axes. However any of the joints may be configured to be pivotable about one, two or three axes at the discretion of the designer. Appropriate changes to the layout of the components of a motion transfer system, which is described below, would be required to accommodate such changes in the rotational capability of the joints.

Referring back to FIGS. 1 and 7, each handle assembly 52 is connected to the wrist joint by a screw 176 that extends through the handle bar 70 and the handle half 72 and into the center half 158. Dowel pins 190 extending into the handle half and the center half provide additional stability to the connection. Screws 192 connect the handlebars to their respective handle halves 72.

Returning now to FIG. 8, the yoke 104 at the upper end of the lower arm embrace the elbow ring 100 at the lower end of the upper arm. The arm pivot 162 extends laterally beyond the bore 160 of the elbow ring and axially into the large hole 106 on the right flank of the yoke. A screw 194 extending through hole 108 on the left flank of the yoke connects the lower arm to the arm pivot.

Referring to FIGS. 9A, 9B, 10A and 10B, the mount 58 includes a lateral slide tube 200 extending axially through a bore in the ball pivot sliding shaft 168 at the shoulder joint 66. A slide lock 202 comprises a stud 204, insert 205, lobed knob 206, and set screw 207. When assembled, the insert resides in a hole 208 in the ball pivot sliding shaft. The stud projects beyond the perimeter of the ball pivot sliding shaft and engages the knob. The illustrated embodiment employs two such slide locks. Tightening of the locks clamps the ball pivot sliding shaft 168 to the slide tube 200 to resist lateral movement of the arm pivot sliding shaft (and therefore of the entire device) relative to the slide tube. Thus, the shoulder joint 66 is selectively slidably engageable with the slide tube and therefore with the mount. The slide lock enables or disables relative motion between the slide tube and the shoulder joint by desecuring or securing the ball pivot shaft relative to the slide tube.

Figure 11:
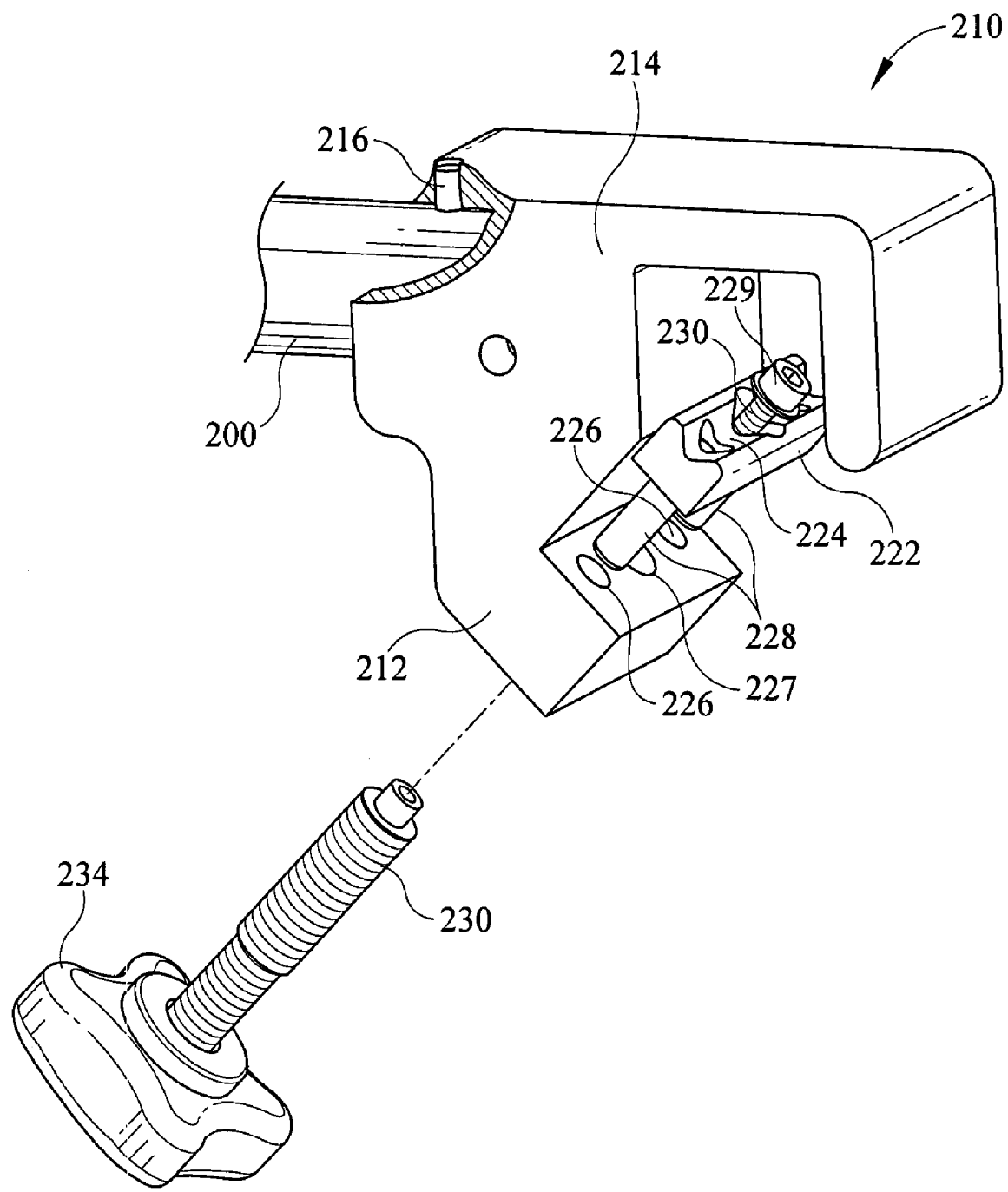
FIG. 11 is a partially exploded perspective view of a frame mount.

Referring additionally to FIG. 11, the mount 58 also includes a frame mount 210. The illustrated embodiment includes left and right frame mounts. Each frame mount includes a leg 212 and a hook 214 connectable to the slide tube 200 with a spring pin 216. The hook is intended to hook onto a rail such as rectangular cross section carbon fiber rail 220 or similar feature on a host device such as an operating table (also see FIGS. 14-17). Each frame mount also includes a frame latch comprising a latch block 222 with a notch 224 therein and guide dowels 228 projecting therefrom. Holes 226 in the leg 212 of the frame mount receive the dowels. A threaded stud 230 extends through central hole 227 in the leg 212 and is connected to the latch block with a screw 229. Knob 234 is attached to the other end of the stud 230. Tightening or loosening the knob moves the latch block into or out of engagement with the rail 220.

Referring to FIGS. 12A-13C, the support and positioning device 50 also includes a coupler 240 for receiving an attachment feature 266 of an accessory. The coupler is secured to a connector plate 241, which is secured to the handle halves 72. The coupler includes a cone housing 242 having a substantially frustoconical cavity 244 and a jaw 246 radially deployable into and radially retractable out of the cavity. The illustrated jaw is a pair of half-jaws, 246L, 246R, each pivotably connected to the housing at a pivot 248 and each independently radially deployable into and retractable out of the cavity. Coil springs 250 secured in place by caps 251 bias the jaw halves to their deployed positions. As explained below, the jaw halves engage the attachment feature 266 to resist withdrawal thereof from the cavity. The cone housing 242 includes an internal flange 252 for governing the axial location of the attachment feature relative to the housing and an internal flat 254 (comprising circumferentially opposite flat surfaces, one of which is visible as 254a) for governing the angular orientation of the attachment feature relative to the housing. The coupler also includes a mechanism engageable with the attachment feature to augment the jaw halves in resisting withdrawal of the attachment feature from the housing when the coupling is in the mated state, i.e. when the attachment feature is mated with the cone housing. In the illustrated device, the mechanism is a locking knob 256 and an associated shank 258 engageable with a recess 259 in the attachment feature.

Figure 14:
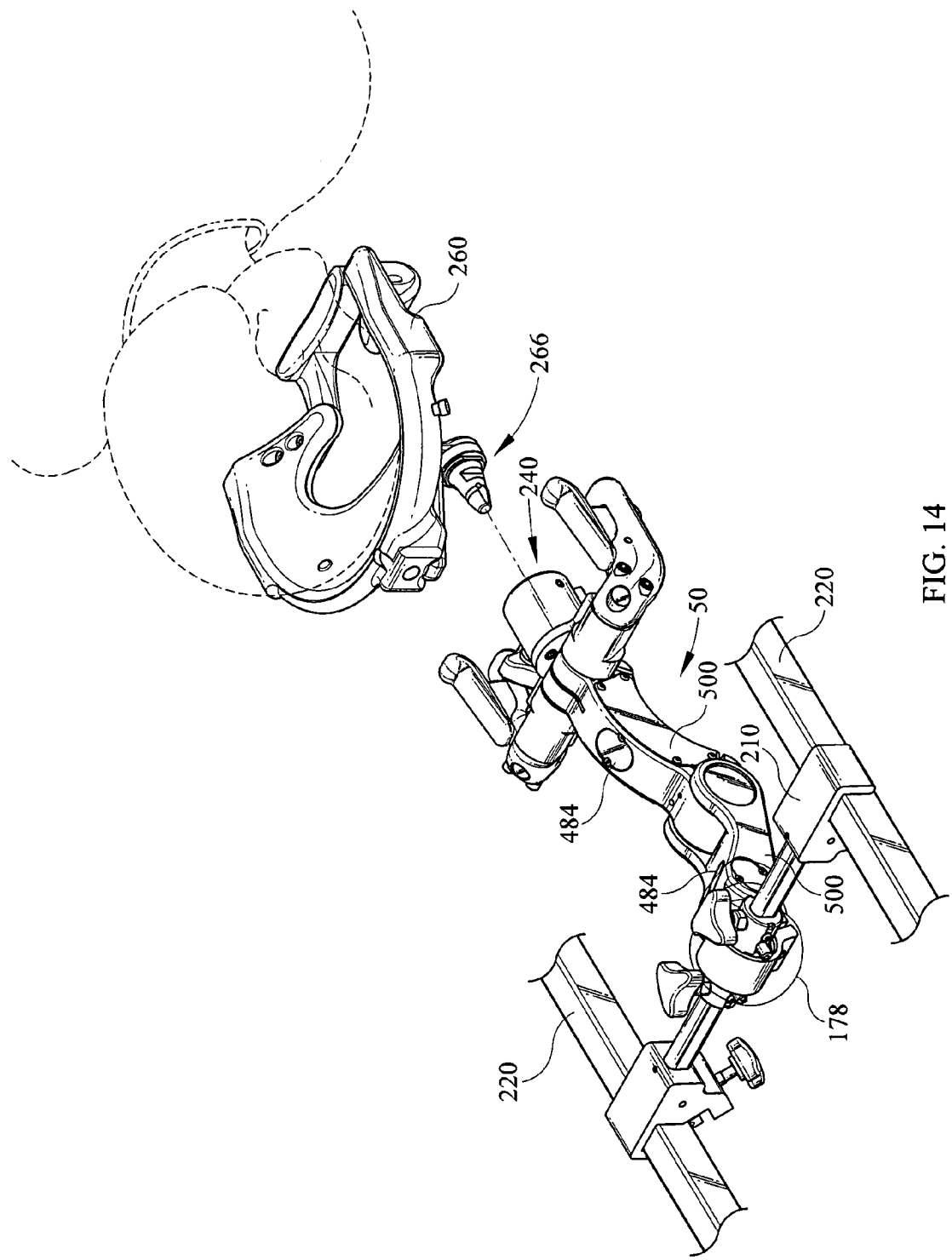
FIGS. 14-17 are perspective views similar to FIG. 1 showing various accessories attachable to the support and positioning device. A patient's head and shoulders are illustrated in phantom in FIG. 14 to show the patient's orientation relative to the support and positioning device.
Figure 15:
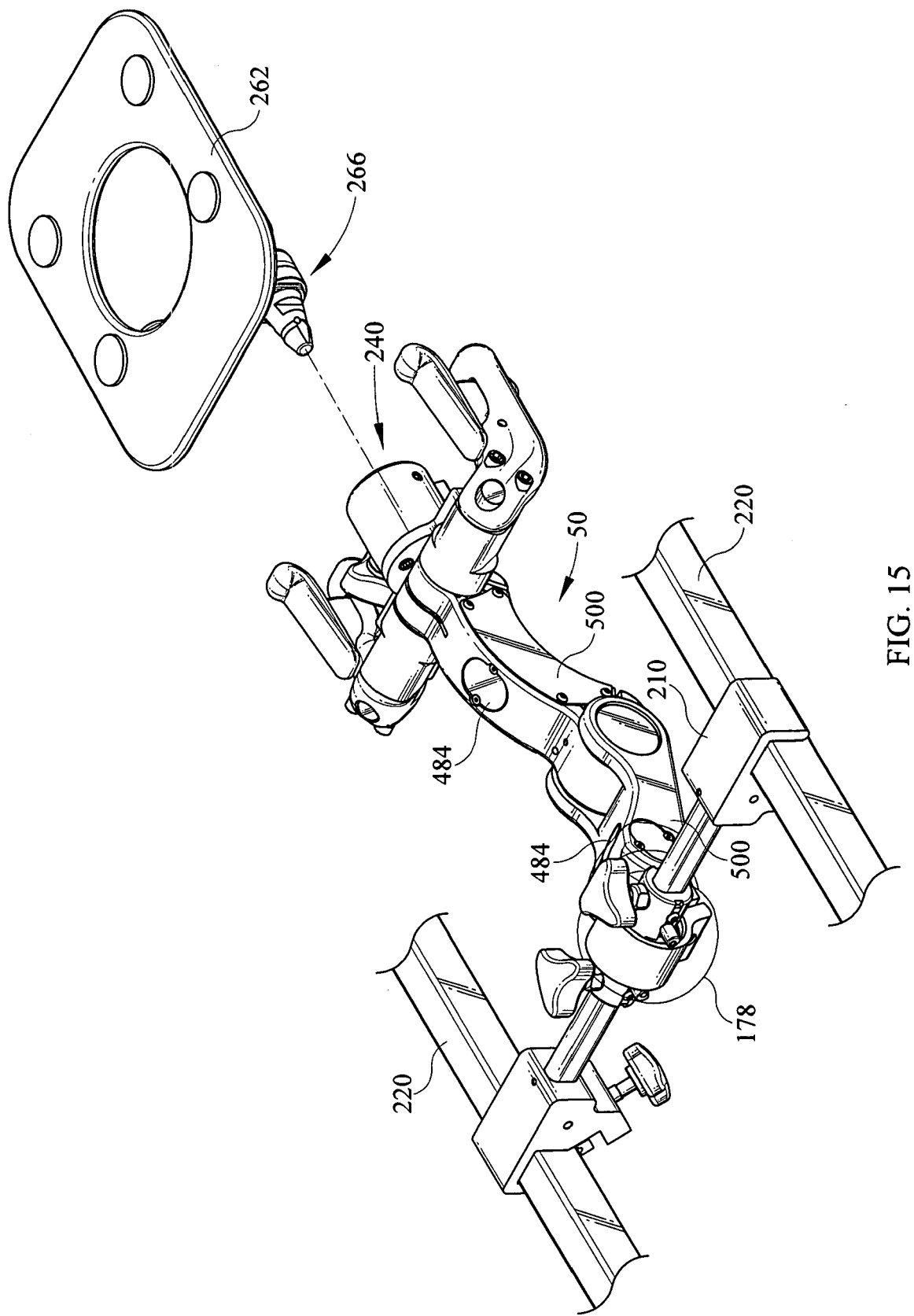
Figure 16:
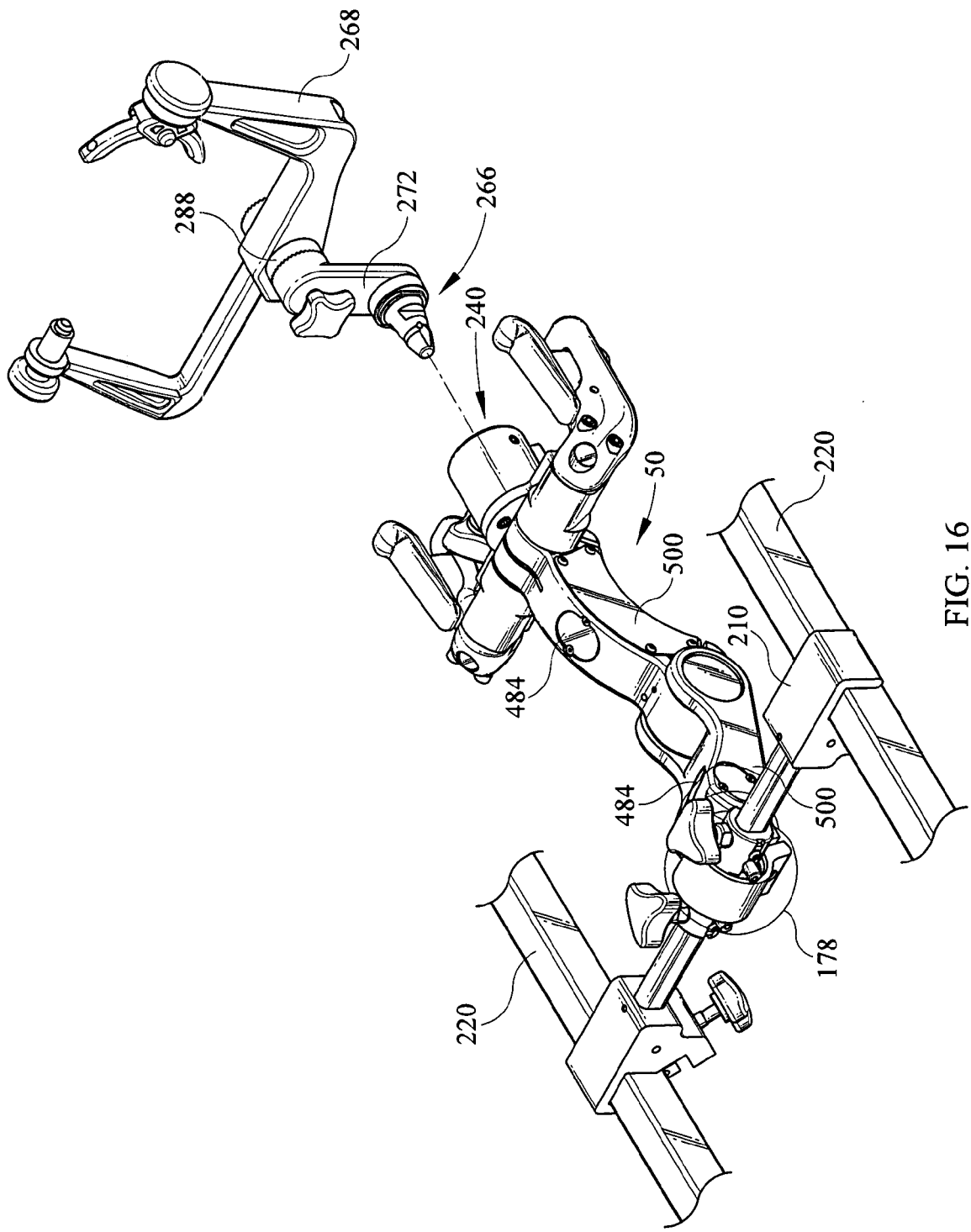
Figure 17:
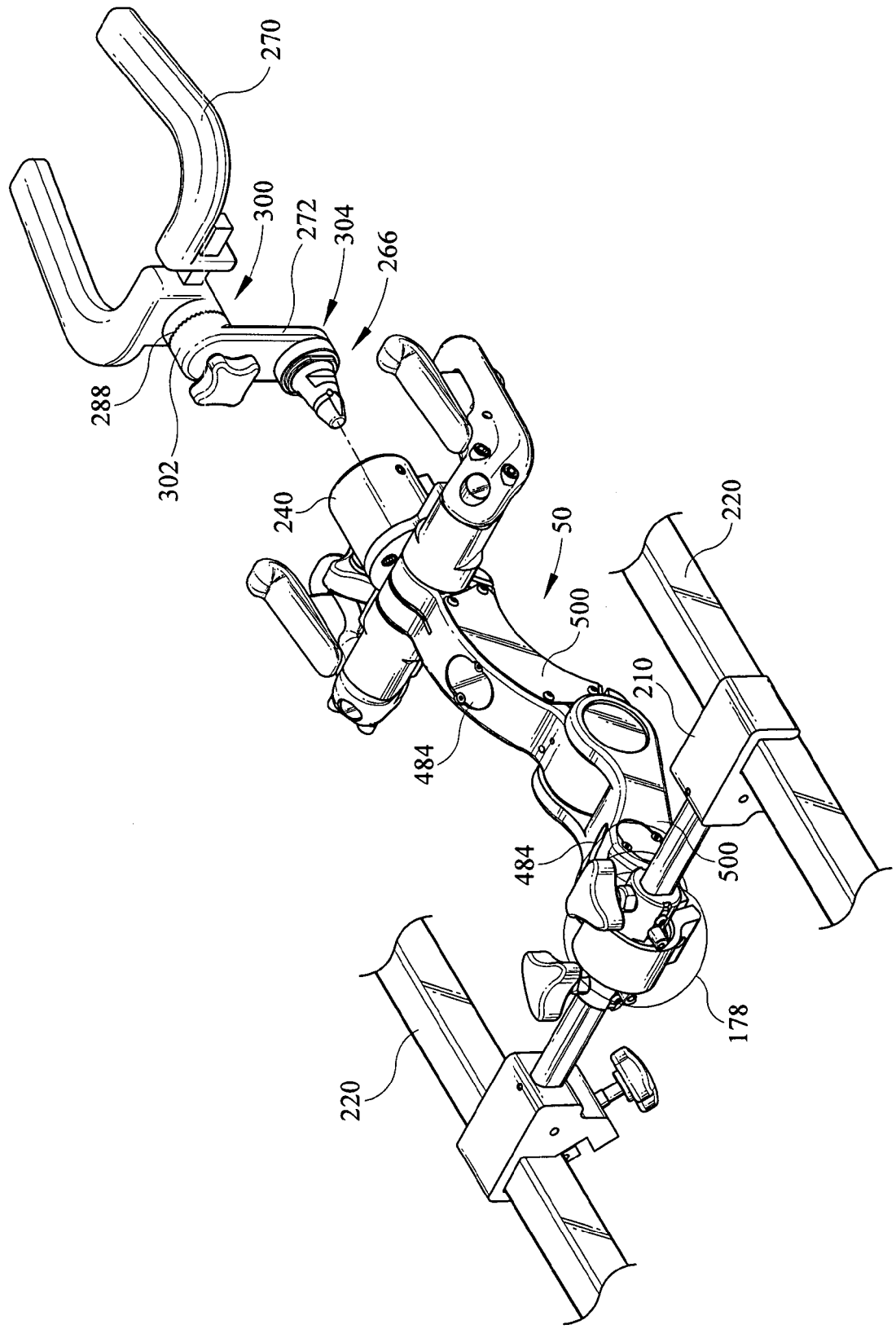
Figure 18:
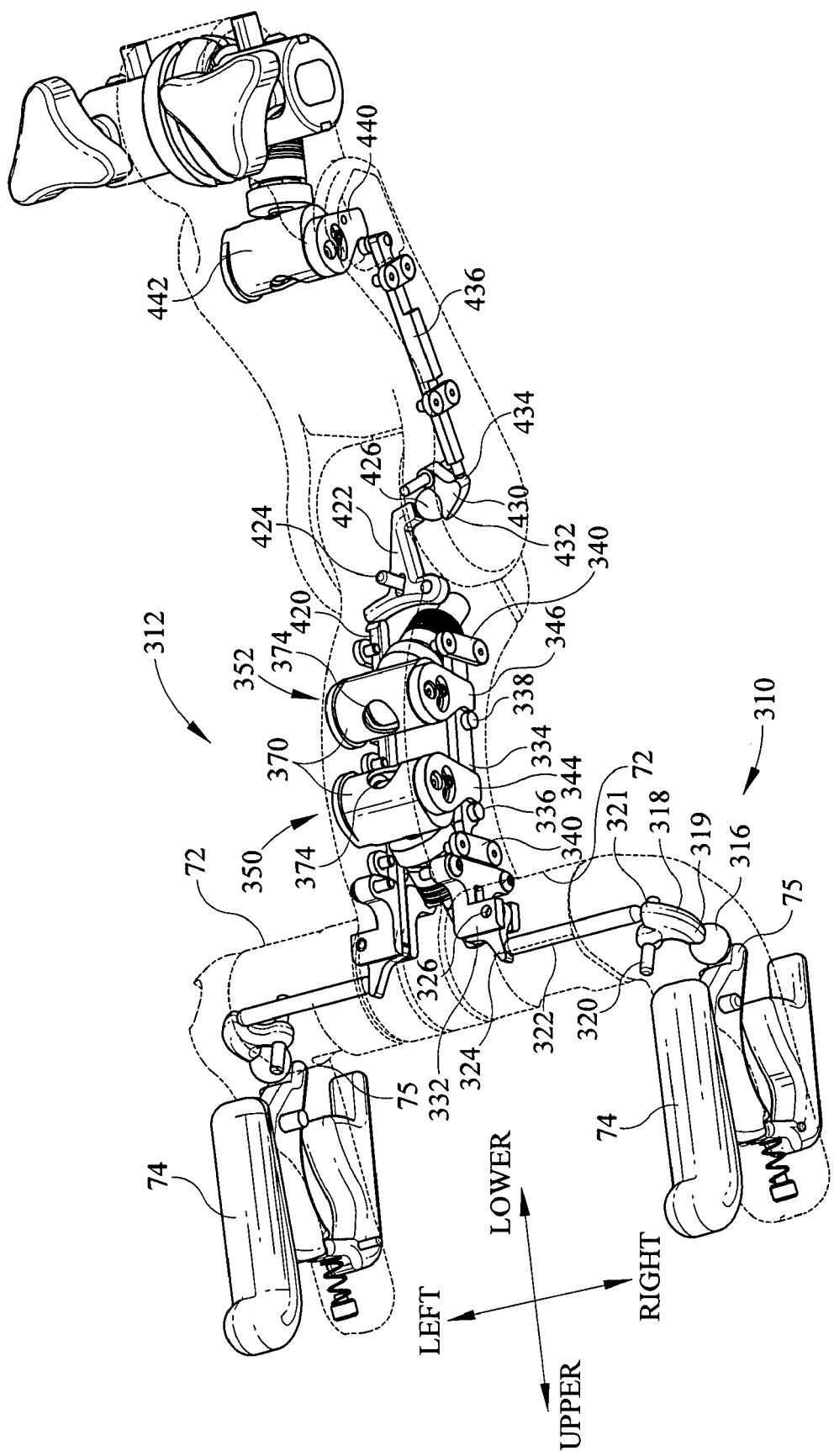
FIG. 18 is a top perspective view of the support and positioning device with exterior components depicted in phantom to reveal components of left and right motion transfer systems.
Figure 19:
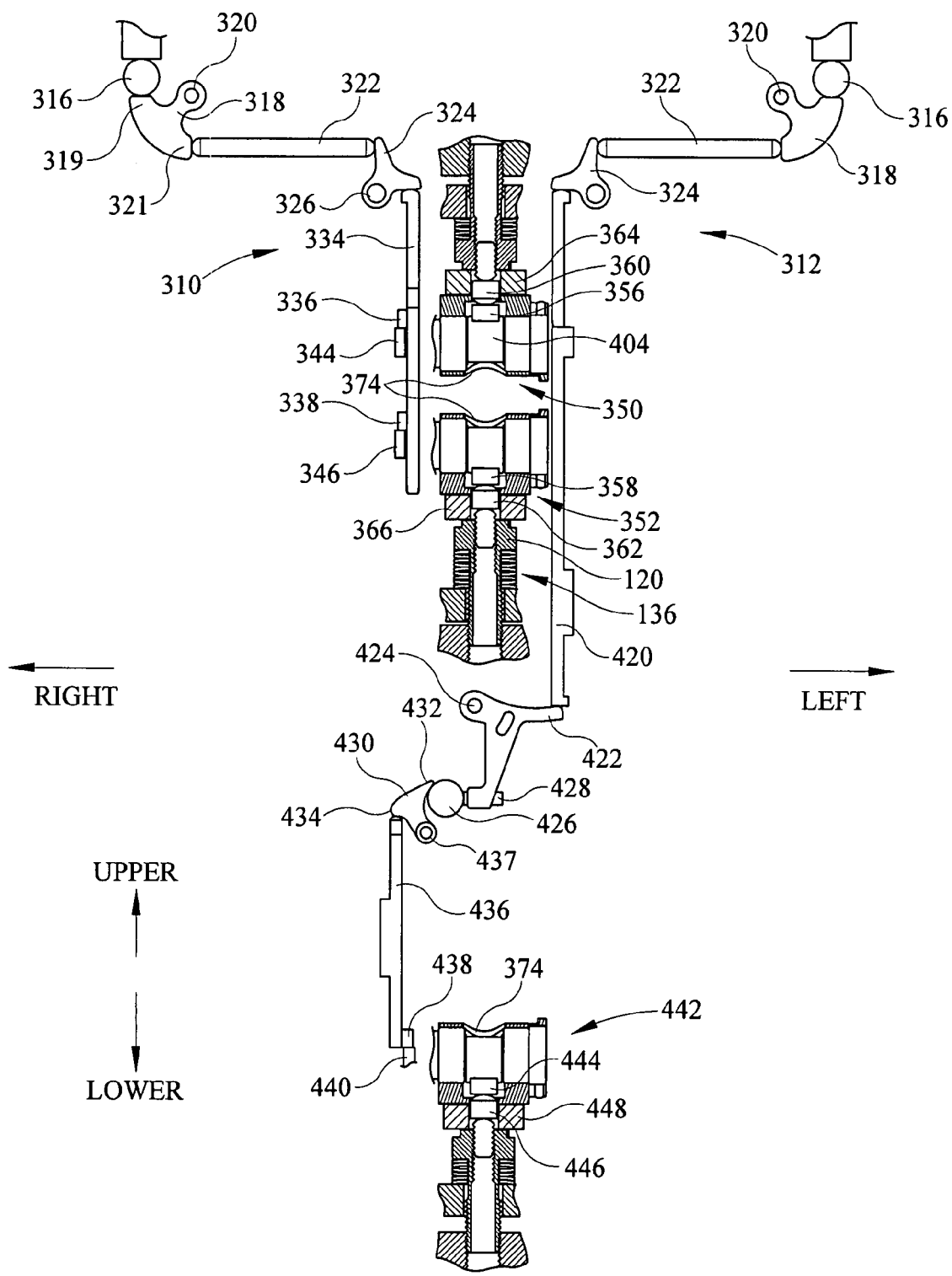
FIG. 19 is a schematic view showing the components of the left and right motion transfer systems of FIG. 18.

Typical accessories attachable to the support and positioning device 50 by way of the coupler 240 include a head engagement module for providing support and/or fixation of a patient's head during surgery. As seen in FIGS. 14 and 15, the head engagement module may be selected from the group consisting of a mask 260 and a flat plate 262. Both the mask and the flat plate have an integral attachment feature 266 that mates with coupler 240 to attach the mask or plate to the support and positioning device 50. As seen in FIGS. 16 and 17, the head engagement module may be also be selected from the group consisting of a skull clamp 268 and a horseshoe head support 270. Neither the skull clamp nor the horseshoe support have an integral attachment feature. Instead, and as seen in FIGS. 16 and 17, the attachment feature 266 is part of a secondary accessory, specifically an adaptor 272, which is removable from the skull clamp or horseshoe support.

Referring to FIGS. 12-17, but principally to FIGS. 12-13, the attachment feature 266 of the mask 260, flat plate 262 and adaptor 272 is an attachment cone 276 comprising a substantially frustoconical cone core 278 with a pair of circumferentially opposed capture slots 280. The cone core includes a shoulder 282 and an external flat 284 comprising a pair of flat surfaces 284L, 284R. The shoulder 282 and flat 284 cooperate with the flange 252 and internal flat 254 of the coupler to govern the axial location and angular orientation of the cone core 278 relative to the housing 242 of the coupler 240.

Figures 12A, 12B:
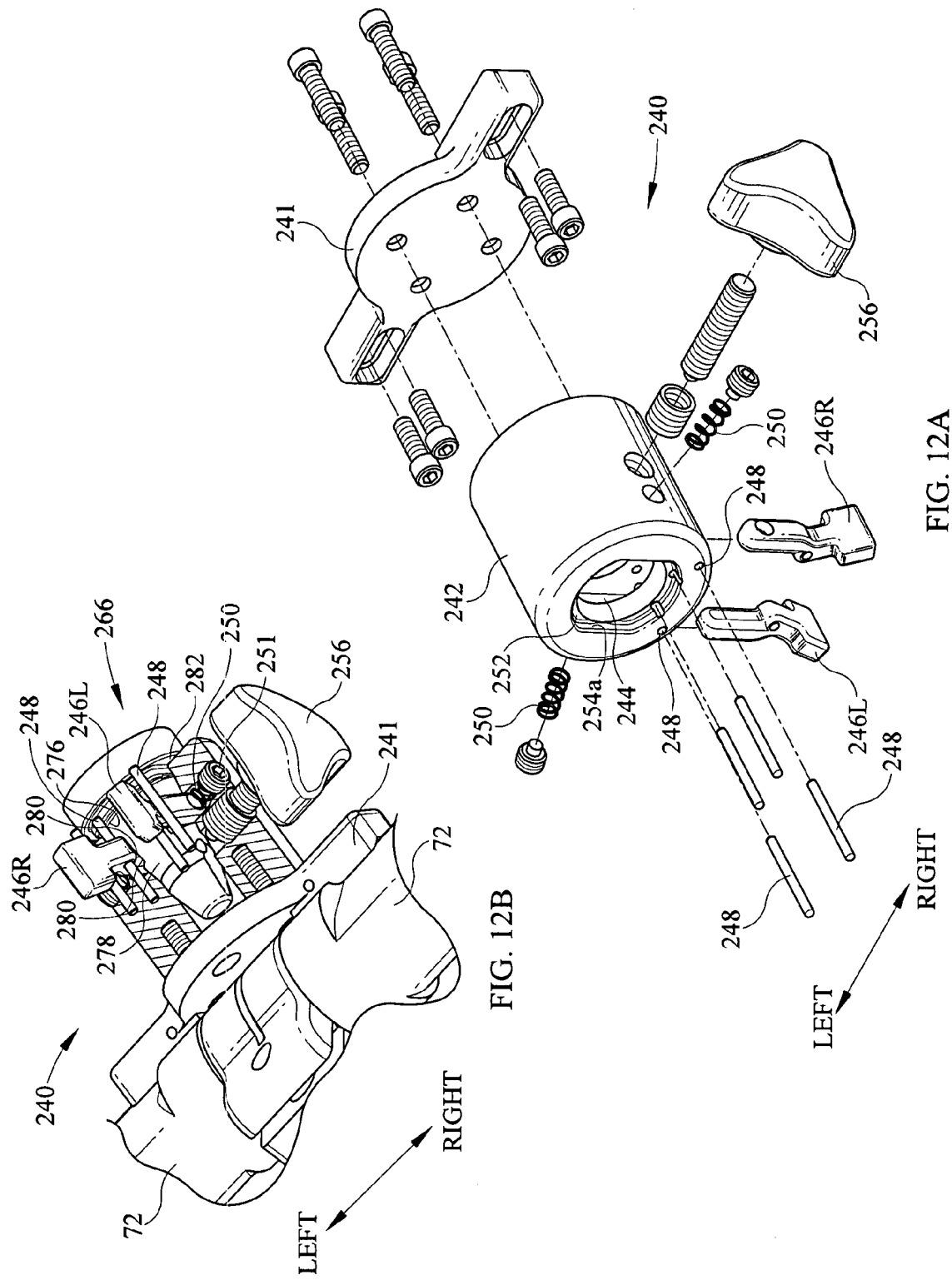
FIG. 12A is an exploded view showing a coupler and a connector plate for connecting the coupler to a handle assembly.
FIG. 12B is a view related to FIG. 12A showing the components assembled together and connected to a handle assembly, the view of FIG. 12B being rotated 180 degrees about the LEFT-RIGHT axis of FIG. 12A.
Figure 13A:
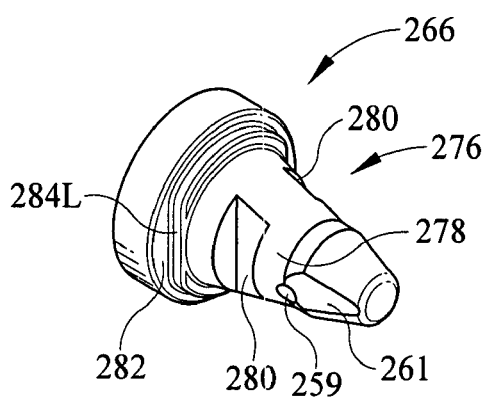
FIGS. 13A and 13B are a perspective view of an attachment and a cross sectional side elevation view of a coupling comprising an attachment mated to the coupler.
Figure 13B:
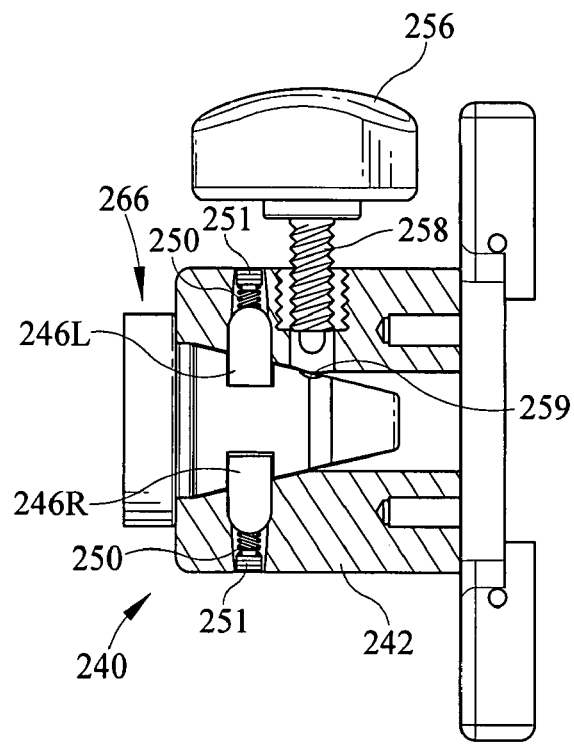
Figure 13C:
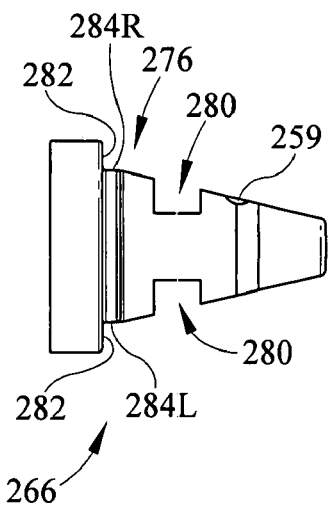
FIG. 13C is a cross sectional side elevational view of the attachment and coupler in an unmated state.
Figure 13C:
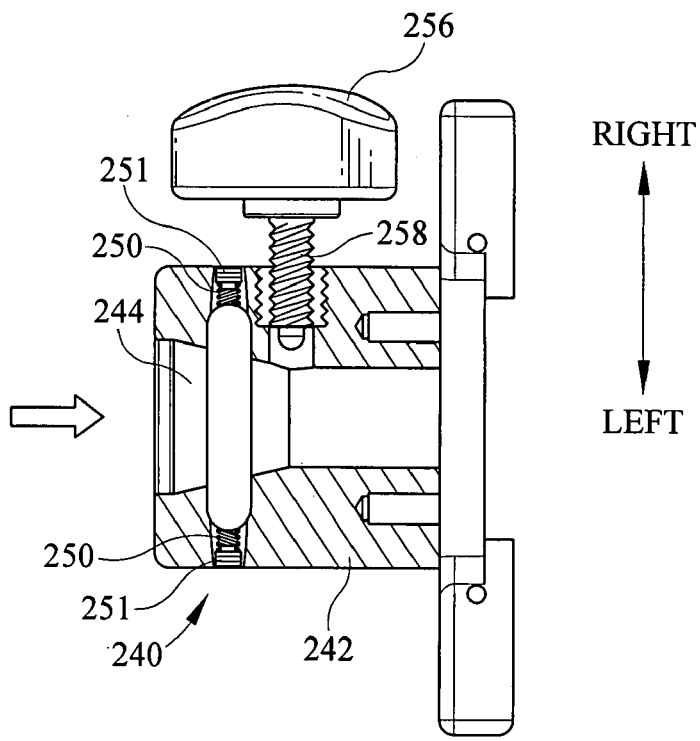

Taken together, the coupler and attachment feature define a coupling for securing an accessory to a host component. Examples of such accessories include the mask 260, flat plate 262 and adaptor 272 discussed above. The coupler is associated with either the accessory or the host component while the attachment feature is associated with the other of the accessory and the host component. In the illustrated configuration, the coupler is associated with the host component 50 while the attachment feature is associated with the accessory. When the coupler and attachment feature are mated together, the attachment feature nests radially inside the housing cavity with each jaw half residing in one of the capture slots to resist withdrawal of the attachment feature from the housing cavity (FIGS. 12B, 13B). The shank 258, extending from the locking knob 256 engages recess 259 in the attachment feature to urge the attachment feature laterally against the opposite side of the cavity thereby augmenting the withdrawal resistance action of the jaws. This locking mechanism also guards against unintended release of the accessory from the host component in the event that the jaw halves were to be inadvertently retracted from the cavity.

The profile of the attachment feature is such that progressive axial insertion of the attachment feature into the cavity urges the jaw halves toward a retracted state until the capture slots are aligned with the jaw halves, at which time the jaw halves snap into the capture slots. In the specific coupling illustrated, it is the substantially frustoconical geometry of the attachment feature and the facets 261 (one of which is visible in FIG. 13A) that urge the jaw halves out of the way during insertion of the attachment feature into the coupler cavity.

As noted previously, certain accessories such as the mask 260 and flat plate 262 attach directly to the support and positioning device 50. Other accessories, such as the horseshoe headrest 270 and skull clamp 268 attach indirectly to the device by way of an adaptor 272. In general, the adaptor 272 adapts an accessory to be secured to a host component, such as the support and positioning device 50. Such adaptation is necessary when the host component has a receptor, such as the coupler 240 and the accessory has an attachment element not compatible with the receptor. Examples of incompatible attachment elements include the sawtooth ring 288 of the horseshoe support and skull clamp. The adaptor has an attachment end 300 with a receiver 302 compatible with the accessory attachment element 288 and a host component end 304 with an attachment feature 266 compatible with the receptor.

The device also includes a release system comprising the previously described operator interface and a motion transfer system extending from the operator interface to each of the three joint locks. The motion transfer system operates the locks by exerting or removing a force $F_A$ thereby unlocking and locking the joints in response to operation of the operator interface.

Referring principally to FIGS. 18-20B, but also to FIGS. 3A-3B, the motion transfer system includes a right motion transfer system 310 and a left motion transfer system 312. The right motion transfer system 310 includes the following serially arranged components:

1. A ball bearing 316 residing in the handlebar.
2. A handle bellcrank 318 pivotably mounted inside the handlebar by pivot 320.
3. A handlebar pin 322, also visible in FIG. 7, extending laterally through the handle half 72.
4. A hook bellcrank 324 pivotably mounted by pivot 326 to an extension leg 332. The extension leg is mounted by screws to a recess 333 (FIG. 7) in the upper arm.
5. A dual pushrod 334 with a wrist lug 336 and an elbow lug 338 projecting laterally therefrom. Clips 340 and screws 342 (FIG. 7) trap the pushrod laterally in a slot 344 extending longitudinally along the right flank of the upper arm, but permit the pushrod to slide longitudinally a limited amount.
6. A wrist paddle 344 and an elbow paddle 346.
7. A wrist cam assembly 350 located inside the upper end of the upper arm near the wrist ring 98 and having the wrist paddle 344 co-rotationally mounted to a cam rod component of the wrist cam assembly. The wrist cam assembly includes a cam sleeve 370 with a pair of windows 372, 374.
8. An elbow cam assembly 352, located inside the lower end of the upper arm near the elbow ring 100 and having the elbow paddle 346 co-rotationally mounted to a cam rod component of the elbow cam assembly. The elbow cam assembly includes a cam sleeve 370 with a pair of windows 372, 374.
9. A wrist cam follower 356 and an elbow cam follower 358.
10. A wrist cam pin 360 and an elbow cam pin 362. Each pin projects radially inwardly through cam sleeve window 372 in the respective cam sleeve to contact the follower. A cam pin guide 364, 366 circumscribes each cam pin.

Figure 20A:
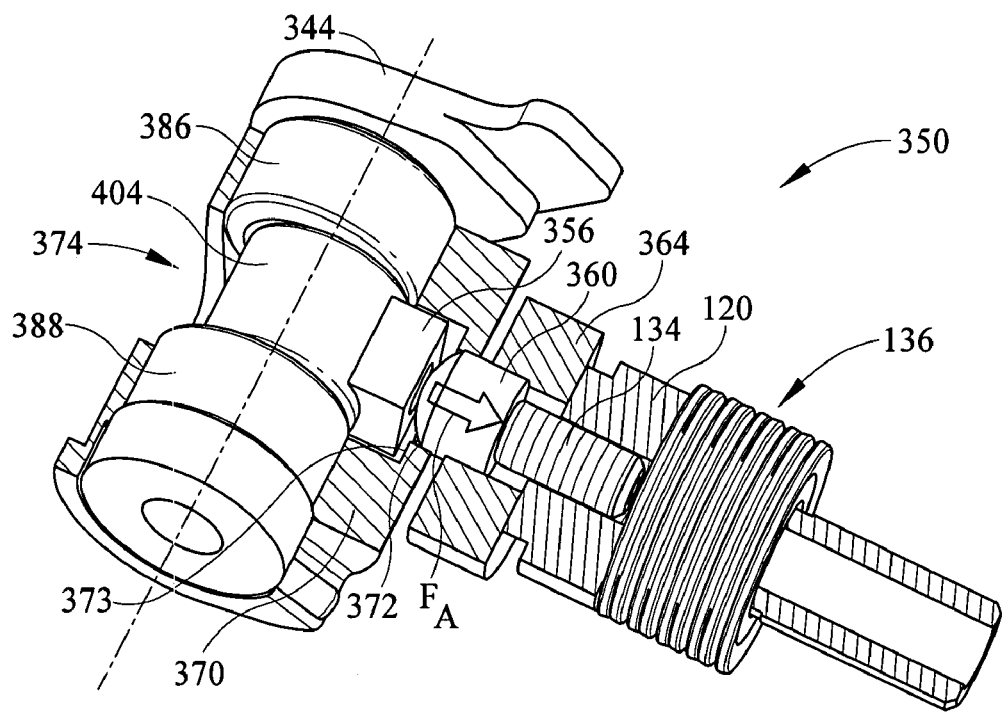
FIG. 20A is a partially cut away perspective view of a representative cam assembly and adjacent components for the device of FIG. 1.
Figure 20B:
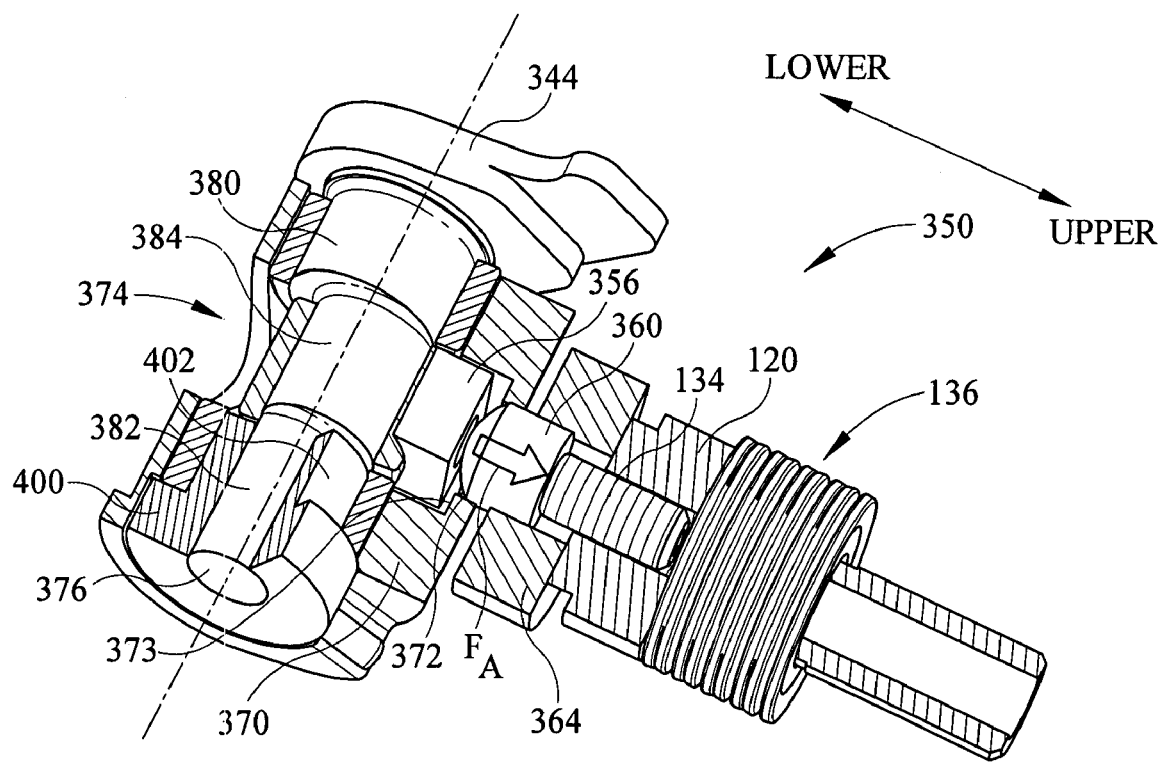
FIG. 20B is a view similar to FIG. 20A with cam rod bearings cut away to expose a cam rod.

Referring principally to FIGS. 20A and 20B additional details of a representative cam assembly, such as wrist cam assembly 350 are evident. The cam assemblies are similar to each other. Accordingly, an explanation of the wrist cam assembly suffices to explain the structure and function of the elbow cam assembly. The wrist cam assembly includes a cam sleeve 370 with a pair of windows 372, 374. Window 374 in the cam sleeve is present only to facilitate machining of interior features of the sleeve, however window 372 allows for motion transfer radially through the cam sleeve. A cam rod 376 extends axially (i.e. laterally) through the cam sleeve. The cam rod has a large diameter section 380, and a small diameter section 382 coaxial with the large diameter section and axially offset therefrom. The cam rod also includes a medial section 384 axially intermediate the large and small diameter sections. The medial section is radially offset from the small and large diameter sections. First and second bearings 386, 388, circumscribe the large and small diameter sections of the cam rod. The bearings are press fit into the cam sleeve and therefore are rotationally fixed relative to sleeve. Because the second bearing 388 has the same dimensions as the first bearing, the second bearing is radially oversized relative to the small diameter section 382 of the cam rod. Accordingly, the cam assembly also includes an end bearing 400 with an axially extending, annular plug 402. The plug occupies the annulus between the second bearing and the small diameter section of the cam rod. The wrist cam assembly also includes a medial bearing 404 circumscribing the radially offset, medial section 384 of the cam rod and located radially between the cam rod and the cam sleeve.

As already noted, the wrist and elbow joints are normally locked, i.e. the wrist and elbow rings grip joint components in the ring bores to immobilize the joints. However, when the right handle lever 74 rotates in response to an operator applied force $F_1$, a tail 75 on the handle lever urges ball bearing 316 against an input leg 319 of the handle bellcrank thus rotating the bellcrank and causing its output leg 321 to move laterally inwardly. The laterally inward motion of the output leg is conveyed to the handle bar pin 322 which translates laterally to rotate the hook bellcrank 324 about pivot 326. The hook bellcrank pushes longitudinally on the dual pushrod 334 to translate it longitudinally downwardly along the upper arm. The lugs 336, 338 rotate the paddles 344, 346 which act upon the cam assemblies 350, 352. Referring specifically to the wrist cam assembly 350, the wrist paddle 344 rotates the wrist cam rod 376 to which it is attached. Because of the radial offset of the medial section of the cam rod, rotation of the cam rod causes the medial bearing to translate radially, i.e. longitudinally upwardly. The motion of the bearing is communicated to the follower 356 and cam pin 360 to exert a force $F_A$ on the set screw 134 projecting from bolt 120. It will be appreciated that $F_A$ is merely a generic indicator of the applied force; the magnitude of the force is not necessarily the same at all the joints. The force $F_A$ compresses the array 136 of spring washers. As a result, and as seen best in FIGS. 4A and 4B, the bolt translates relative to the hole 114 in the proximal flange, thereby forcing the distal flange 112 away from the proximal flange and opening the interflange gap 124. Accordingly, the wrist ring loosens its grip on the joint components housed in the bore 113 of the wrist ring 98, thus unlocking the wrist joint and allowing the joint to be articulated.

Concurrently and similarly, the elbow lug 338 rotates elbow paddle 346 to communicate the motion of the dual pushrod to the elbow cam assembly and ultimately to the elbow joint. The kinematics are the same as has already been described for the wrist joint, except that the medial bearing, cam follow and pin move longitudinally downwardly, rather than upwardly.

The left motion transfer system 312 includes the following serially arranged components, the first four of which are left hand counterparts of the components of the right motion transfer system. Counterpart or substantially similar components are identified with the same reference numerals as have already been used for the components of the right motion transfer system.

1. A ball bearing 316 residing in the handlebar.
2. A handle bellcrank 318 pivotably mounted inside the handlebar by pivot 320.
3. A handlebar pin 322, also visible in FIGS. 3A, 3B and 7, extending laterally through the handle half 72.
4. A hook bellcrank 324 pivotably mounted by pivot 326 to an extension leg 332. The extension leg is mounted by screws to a recess 333 (FIG. 7) in the upper arm.
5. A long pushrod 420 also visible in FIG. 8. Clips and screws 340, 342 (FIG. 7) trap the pushrod laterally in a slot extending longitudinally along the left flank of the upper arm, but permit the pushrod to slide longitudinally a limited amount.
6. Referring additionally to FIG. 8, an arm rocker bellcrank 422 pivotably connected at pivot 424 to the upper arm and projecting longitudinally into the arm pivot 162, which is circumscribed by the elbow ring 100. An oval "point" set screw 428 (visible in FIG. 19) projects through an opening in the foot of the bellcrank.
7. A bearing ball 426 in the arm pivot 162 adjacent to the arm rocker bellcrank 422 and in contact with the point of the set screw in the foot of the bellcrank.
8. A pivot rocker bellcrank 430 in the arm pivot 162. The pivot rocker bellcrank has a heel 432 adjacent to the bearing ball and a toe 434. The pivot rocker bellcrank is pivotable about pivot 437.
9. An end pushrod 436 with a lug 438 projecting laterally therefrom. Clips and screws similar to clips and screws 340, 342 (FIG. 7) trap the end pushrod laterally in a slot extending longitudinally along the right flank of the upper arm, but permit the pushrod to slide longitudinally a limited amount.
10. A shoulder paddle 440 similar to the wrist and elbow paddles 344, 346.
11. A shoulder cam assembly 442 located inside the lower end of the lower arm near the shoulder ring and having the shoulder paddle 440 co-rotationally mounted to a cam rod component of the shoulder cam assembly. The assembly includes a cam sleeve 370 with a pair of windows 372, 374.
12. A shoulder cam follower 444.
13. A shoulder cam pin 446 circumscribed by a cam pin guide 448. Each pin projects radially inwardly through cam sleeve window 372 to contact the follower.

As already noted, the shoulder joint is normally locked, i.e. the shoulder ring grips joint components in the ring bore to immobilize the joint. However, when the left handle lever rotates in response to an operator applied force $F_1$, a tail on the lever urges ball bearing 316 against an input leg 319 of the handle bellcrank 318 thus rotating the bellcrank and causing its output leg 321 to move laterally inwardly. The laterally inward motion of the output leg is conveyed to the handle bar pin 322 which translates laterally to rotate the hook bellcrank 324 about pivot 326. The hook bellcrank pushes laterally on the long pushrod 420 to translate it downwardly along the upper arm. The long pushrod rotates the arm rocker bellcrank 422 about pivot 424, thus urging the bearing ball 426 laterally against the heel 432 of the pivot rocker bellcrank. In response, the pivot rocker bellcrank rotates about its pivot axis 437 and urges the end pushrod longitudinally (i.e. downwardly). Lug 438 at the lower end of the pushrod rotates the shoulder paddle 440, which acts upon the shoulder cam assembly 442. The kinematics from the shoulder cam assembly to the shoulder lock are that same as has already been described for the wrist joint. As a result, the shoulder ring loosens its grip on the joint components housed in the bore of the shoulder ring, thus unlocking the shoulder joint and allowing it to be articulated.

Although the illustrated device is configured so that the right release system operates the wrist and elbow joints and the left release system operates the shoulder joints, the mechanism could be configured so that the right release system operates the shoulder joint and the left release system operates the wrist and elbow joints. In general, the linkages can be arranged so that the right and left release systems operate mutually exclusive, collectively exhaustive subsets of the deformable rings 98, 100, 102 to lock and unlock the corresponding wrist, elbow and shoulder joints 62, 64, 66. In the limit, either the right or left release system could operate all three rings, in which case the other release system could be dispensed with. In another configuration, all three rings could be operable by both release systems, giving the operator a choice of which release system (left or right) to use at any particular time.

As is evident from the foregoing, part of the motion transfer system (the right motion transfer system in the illustrated device) extends from the handle assembly to the upper arm to control locking and unlocking of the wrist and elbow joints and another part of the motion transfer system (the left motion transfer system in the illustrated device) extends from the handle assembly to the lower arm by way of the upper arm and the bore of the elbow ring to control locking and unlocking of the shoulder joint.

The above described motion transfer system is a mechanical linkage comprising specific types of mechanical elements such as levers, bellcranks, cams, pushrods and the like. However the device may also be configured to operate in response to other types of mechanical elements including, by way of example only, pneumatic elements and hydraulic elements. Moreover, although the illustrated device transfers a compressive force from the operator interface to the locks associated with rings 98, 100, 102, the motion transfer system could instead be configured to employ tensile elements, such as cables, to achieve the desired result. The device may also use non-mechanical elements, such as electrical or electromechanical devices instead of or in combination with mechanical elements.

In view of the foregoing description, certain aspects of the device can now be appreciated. The device has at least two joints, each of which has a locked state and an unlocked state. The release system allows an operator to select between the locked and unlocked states. The device itself has a rest state corresponding to a condition in which all the joints are locked and an active state corresponding to a condition in which at least one joint is unlocked. Moreover, the operator interface is conveniently located remotely from the joints and at a location where the operator can support the weight of the patient's head even when one or more of the joints is unlocked.

Figure 21:
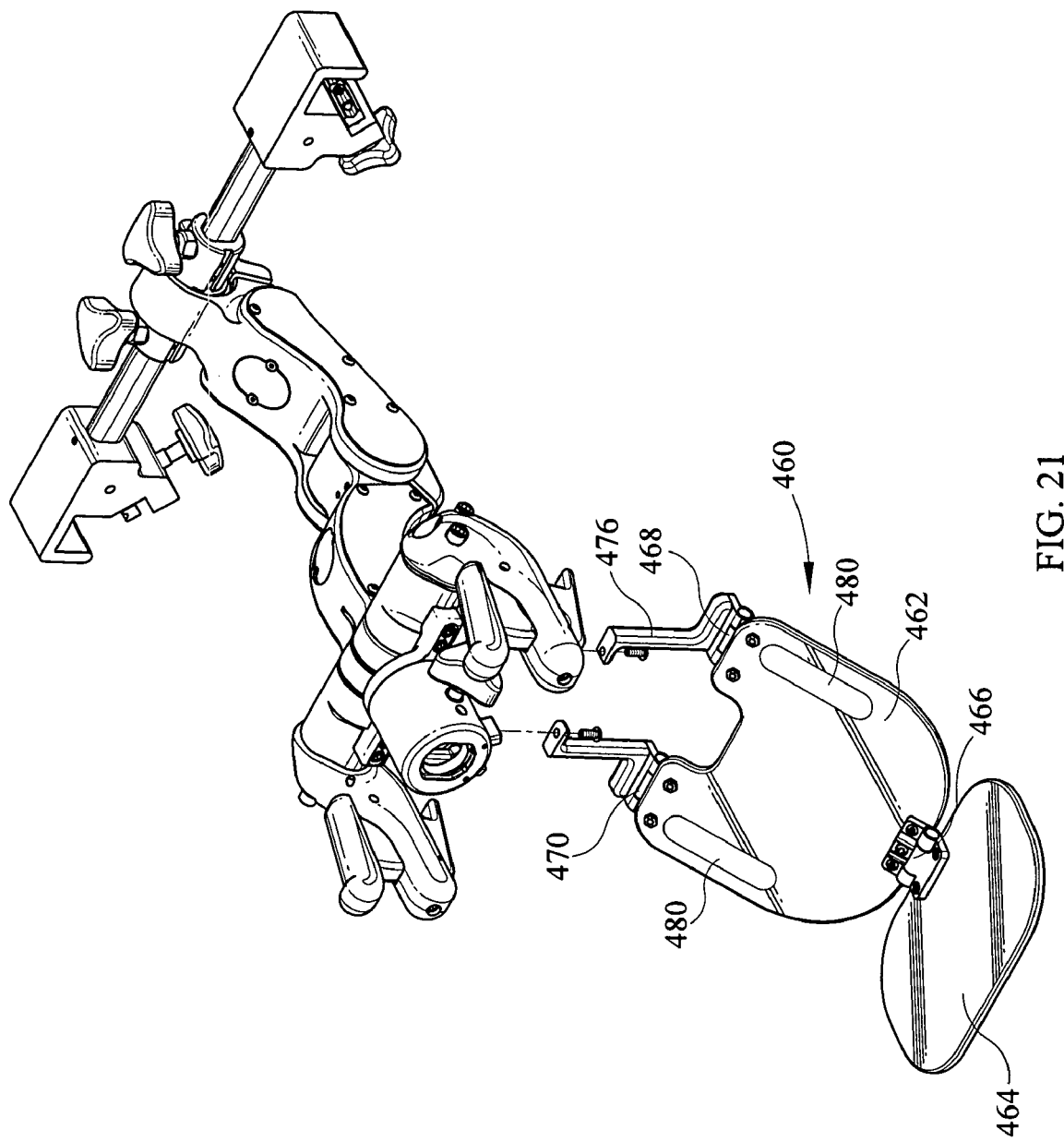
FIG. 21 is a view similar to FIG. 1 showing a mirror assembly attachable to the device.
Figure 22:
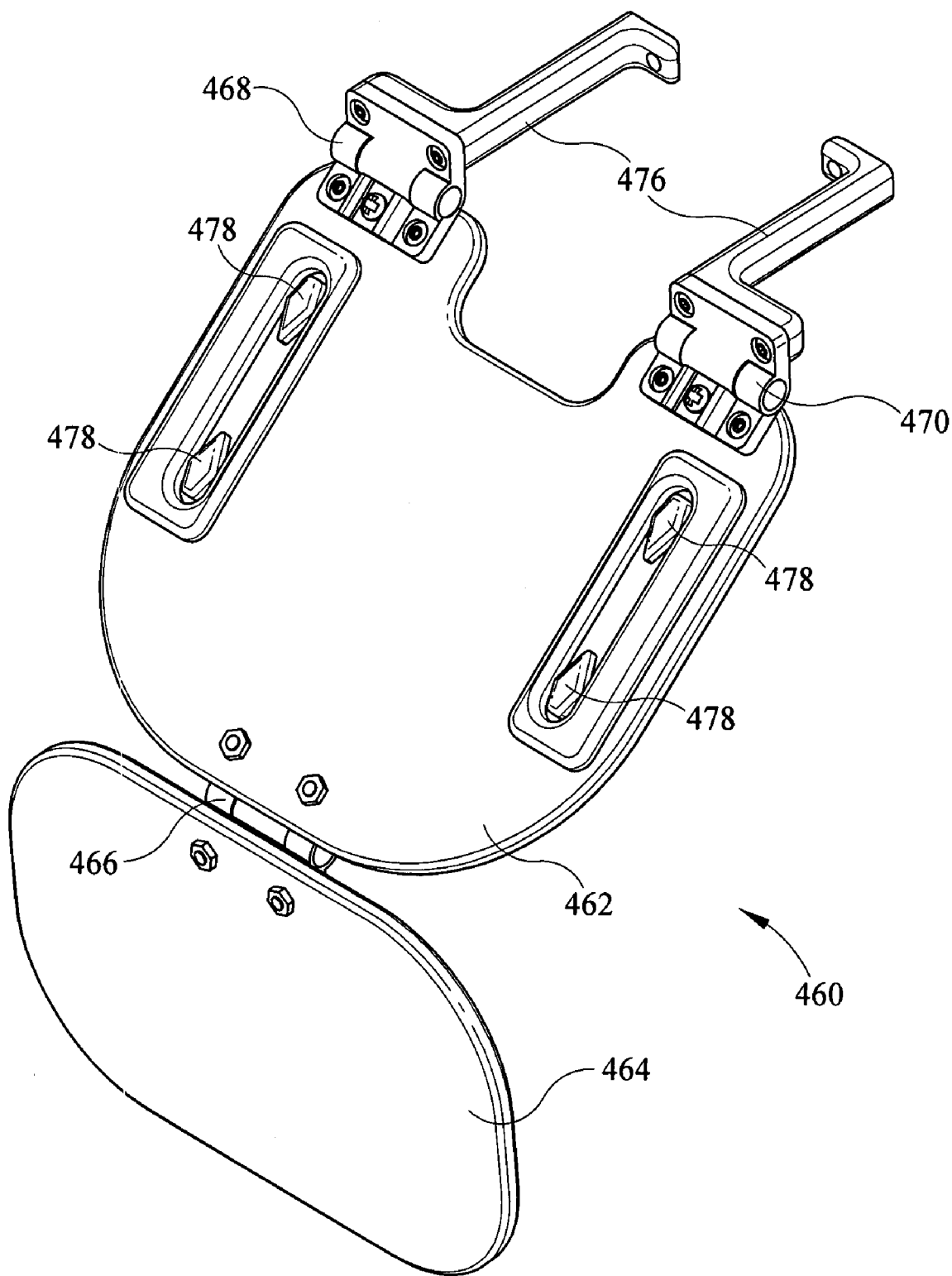
FIG. 22 is a view showing the reverse side of the mirror assembly of FIG. 21.

Referring to FIG. 21, the device may also include a mirror assembly 460. The mirror assembly includes a primary mirror 462 and a secondary mirror 464 connected to the primary mirror by an intermirror hinge 466. Primary mirror hinges 468 470 connect the primary mirror to standoffs 476. The standoffs are each screwed to handle assembly 52 to secure the mirror assembly to the support and positioning device 50, thereby permitting the attending medical staff to observe the face of a patient lying face down and whose head is supported by one of the head engagement modules of FIGS. 14-17.

The illustrated primary mirror also includes one or more lamps 478 on the nonreflective side thereof and corresponding light refractors 480 on the reflective side thereof. During operation, the refractors diffuse light from the lamps to better illuminate the patient's face.

As seen in FIGS. 4A-5B, access ports 482 provide means for accessing the bolts 120 during assembly. Covers 484 (FIGS. 1, 14-17 and 21) are fastened by screws to close the ports. As seen in FIG. 8, openings 488 accommodate installation of the cam assemblies 350, 352, 442. Side covers 500 (FIGS. 1, 7, 8, 14-17 and 21) are screwed to the flanks of the upper and lower arms 54, 56.

To use the device, a member of the medical staff uses frame mount 210 to secure the device to the rails 220 of an operating table. A staff member adjusts the lateral position of the device by loosening the slide locks 202, sliding the device to the desired position along the slide tube 200 and retightening the locks. A staff member attaches a primary accessory such as mask 260 or flat plate 262 directly to the coupler. Alternatively, the staff member attaches a primary accessory such as skull clamp 268 or horseshoe headrest 270 to the coupler indirectly by way of the adaptor 272. Either way, progressive insertion of the attachment feature into coupler cavity 244 pushes the jaw halves 246L, 246R radially outwardly until they snap back into place in the capture slots 280 on either side of the attachment feature. The staffer then tightens the locking mechanism (shank 258 attached to knob 256) to guard against unintended release of the accessory as a result of the jaws being inadvertently retracted. Either before or during surgery, the staff can effect position and orientation adjustment by squeezing the right and/or left interlocks and handle levers to release the joint or joints controlled by the handle levers, thereby allowing articulation of the device as described above. The position and/or orientation adjustments can be made by a single person. Because the handlebar 70 is nearby the head engagement module (260, 266, 268, 270) the staff member can concurrently support the weight of the patient's head while one or more of the joints is in an unlocked state. When the patient's head is at the desired position and orientation, the staff member releases the handle lever or levers. In response, the wrist, elbow and shoulder rings 98, 100, 102 return to their locked state and, in doing so, exert reverse forces through the motion transfer system to return the handle lever to its initial position shown in FIGS. 2 and 3A. The torsion spring 86 assists in returning the handle lever to its initial position.

A member of the medical staff can also separate the mask 260, flat plate 262 or coupler 272 (FIGS. 14-16) from the coupler by loosening the locking mechanism (shank 258 attached to knob 256) and then squeezing the exposed ends of the jaw halves 246L, 246R circumferentially toward each other. Squeezing the jaw halves retracts the jaw halves out of the capture slots 280 in the attachment cone 276, thereby releasing the attachment feature 266.

Although the disclosed device has been described in the context of supporting the head of a human patient during surgery, it may also be adapted for supporting other body parts, may be used as a support during non-surgical procedures and may also find similar uses in veterinary medicine.

We claim:

1. A device for supporting and positioning a part of a patient's body, comprising:
   at least two joints each having a locked state and an unlocked state;
   a release system for allowing an operator to select between the locked state and the unlocked state, the release system having an operator interface remote from the joints and at a location that enables the operator to support the weight of the body part while at least one of the joints is in the unlocked state; and
   a coupler for receiving an attachment feature associated with an accessory, wherein the coupler comprises a cone housing having a substantially frustoconical cavity and a pair of half jaws pivotably connected to the housing and each radially deployable and radially retractable out of the cavity.

2. The device of claim 1 wherein the accessory is a head engagement module.

3. The device of claim 2 wherein the head engagement module is selected from the group consisting of a first group and a second group and where in the first group consists of a mask and a flat plate and wherein the attachment feature is integral with the head engagement module and wherein the second group consists of a skull clamp and a horseshoe head support and wherein the attachment feature is part of an adaptor removable from the head engagement module.

4. The device of claim 1 wherein the attachment feature is an attachment cone comprising a substantially frustoconical cone core with a pair of circumferentially opposed capture slots.

5. The device of claim 1 wherein the device has a rest state corresponding to the locked state of all the joints and an active state corresponding to the unlocked state of at least one joint.

6. The device of claim 1 wherein the patient is a human patient and the part of the patient's body is the patient's head.

7. The device of claim 1 wherein the operator interface comprises a handle lever and an interlock.

8. The device of claim 1 wherein the release system includes a motion transfer system for locking and unlocking the joints in response to operation of the operator interface.

9. The device of claim 8 wherein the motion transfer system is a mechanical linkage.

10. The device of claim 8 wherein the motion transfer system comprises left and right motion transfer systems, and wherein one of the left and right motion transfer systems operates the wrist and elbow rings to lock and unlock the wrist and elbow joints and the other of the left and right motion transfer systems operates the shoulder ring to lock and unlock the shoulder joint.

11. The device of claim 1 including a lock associated with each joint and wherein the release system includes a motion transfer system for operating the locks to lock and unlock the joints in response to operation of the operator interface.

12. The device of claim 1 wherein the operator interface is a component of a handle assembly through which the operator can support the weight of the body part while at least two of the joints are in the unlocked state.

13. The device of claim 1 wherein the operator interface is a component of a handle assembly through which the operator can support the weight of the body part while maintaining at least two of the joints in the unlocked state.

14. The device of claim 13 wherein the handle assembly includes a handlebar and the operator can support the weight of the body by way of the handlebar.

15. The device of claim 1 wherein all of the at least two joints are rotational joints, and the locked and unlocked states are rotationally locked and unlocked states.

16. A device for supporting and positioning a part of a patient's body, comprising:
  at least two joints each having a locked state and an unlocked state;
  a release system for allowing an operator to select between the locked state and the unlocked state, the release system having an operator interface remote from the joints and at a location that enables the operator to support the weight of the body part while at least one of the joints is in the unlocked state; and
  a lower arm extending longitudinally from a shoulder joint to an elbow joint, an upper arm extending from the elbow joint to a wrist joint, and a handle assembly extending laterally from the wrist joint,
  wherein one of the arms includes a shoulder ring circumscribing the shoulder joint, the other of the arms includes a wrist ring circumscribing the wrist joint, and either but not both of the arms includes an elbow ring circumscribing the elbow joint.

17. The device of claim 16 wherein the rings are elastically deformable between a locked state and an unlocked state corresponding respectively to the locked and unlocked states of the joints.

18. The device of claim 16 comprising:
  a right motion transfer system comprising:
  a right ball bearing, a right handle bellcrank, a right handle bar pin, a right hook bellcrank and a dual pushrod responsive to the right handle lever;
  a wrist paddle, a wrist cam assembly, a wrist cam follower and a wrist cam pin responsive to the dual pushrod for locking and unlocking the wrist joint;
  an elbow paddle, an elbow cam assembly, an elbow cam follower and an elbow cam pin responsive to the dual pushrod for locking and unlocking the elbow joint; and
  a left motion transfer system comprising:
  a left ball bearing, a left handle bellcrank, a left handle bar pin, a left hook bellcrank and a long pushrod responsive to a left handle lever;
  an arm rocker bellcrank, a bearing ball, a pivot rocker bellcrank, and end pushrod responsive to the long pushrod; and
  a shoulder paddle, a shoulder cam assembly, a shoulder cam follower and a shoulder cam pin responsive to the end pushrod for locking and unlocking the shoulder joint.

19. The device of claim 16 wherein components of the wrist joint reside in a bore of a wrist ring and comprise a center disk, an axially inner pair of thrust washers bordering the center disk, a pair of thrust bearings bordering the inner pair of thrust washers, an axially outer pair of thrust washers bordering the thrust bearings and a pair of center halves bordering the axially outer thrust washers, the center halves and wrist ring being rotationally fixed relative to each other in the locked state of the wrist joint and rotatable about a bore axis relative to each other in the unlocked state of the wrist joint.

20. The device of claim 16 wherein components of the elbow joint reside in a bore of an elbow ring and comprises an arm, pivot, the arm pivot and elbow ring being rotationally fixed relative to each other in the locked state of the elbow joint and rotatable about a bore axis relative to each other in the unlocked state of the elbow joint.

21. The device of claim 16 wherein components of the shoulder joint reside in a bore of a shoulder ring and include a pivot assembly comprising a two piece ball pivot and a ball pivot shaft secured to the ball pivot, the pivot assembly and the shoulder ring being rotationally fixed relative to each other in the locked state of the shoulder joint and rotatable about a bore axis relative to each other in the unlocked state of the shoulder joint.

22. A device for supporting and positioning a part of a patient's body, comprising:
  at least two joints each having a locked state and an unlocked state;
  a release system for allowing an operator to select between the locked state and the unlocked state, the release system having an operator interface remote from the joints and at a location that enables the operator to support the weight of the body part while at least one of the joints is in the unlocked state, wherein the operator interface includes a left operator interface and a right operator interface, the left and right operator interfaces arranged to operate mutually exclusive, collectively exhaustive subsets of deformable rings to lock and unlock corresponding joints.

23. The device of claim 22 comprising a coupler for receiving an attachment feature associated with an accessory.

24. The device of claim 23 wherein the coupler comprises a cone housing having a substantially frustoconical cavity and a pair of half jaws pivotably connected to the housing and each radially deployable into and radially retractable out of the cavity.

25. The device of claim 24 wherein the accessory is a head engagement module.

26. The device of claim 25 wherein the head engagement module is selected from the group consisting of a first group and a second group and where in the first group consists of a mask and a flat plate and wherein the attachment feature is integral with the head engagement module and wherein the second group consists of a skull clamp and a horseshoe head support and wherein the attachment feature is part of an adaptor removable from the head engagement module.

27. The device of claim 23 wherein the attachment feature is an attachment cone comprising a substantially frustoconical cone core with a pair of circumferentially opposed capture slots.

28. The device of claim 22 wherein the device has a rest state corresponding to the locked state of all the joints and an active state corresponding to the unlocked state of at least one joint.

29. The device of claim 22 wherein the patient is a human patient and the part of the patient's body is the patient's head.

30. The device of claim 22 wherein the operator interface comprises a handle lever and an interlock.

31. The device of claim 22 wherein the release system includes a motion transfer system for locking and unlocking the joints in response to operation of the operator interface.

32. The device of claim 31 wherein the motion transfer system is a mechanical linkage.

33. The device of claim 22 including a lock associated with each joint and wherein the release system includes a motion transfer system for operating the locks to lock and unlock the joints in response to operation of the operator interface.

34. The device of claim 22 comprising a lower arm extending longitudinally from a shoulder joint to an elbow joint, an upper arm extending from the elbow joint to a wrist joint, and a handle assembly extending laterally from the wrist joint.

35. The device of claim 34 wherein one of the arms includes a shoulder ring circumscribing the shoulder joint, the other of the arms includes a wrist ring circumscribing the wrist joint, and either but not both of the arms includes an elbow ring circumscribing the elbow joint.

36. The device of claim 35 wherein the rings are elastically deformable between a locked state and an unlocked state corresponding respectively to the locked and unlocked states of the joints.

37. The device of claim 34 comprising:
a right motion transfer system comprising:
a right ball bearing, a right handle bellcrank, a right handle bar pin, a right hook bellcrank and a dual pushrod responsive to the right handle lever;
a wrist paddle, a wrist cam assembly, a wrist cam follower and a wrist cam pin responsive to the dual pushrod for locking and unlocking the wrist joint;
an elbow paddle, an elbow cam assembly, an elbow cam follower and an elbow cam pin responsive to the dual pushrod for locking and unlocking the elbow joint; and
a left motion transfer system comprising:
a left ball bearing, a left handle bellcrank, a left handle bar pin, a left hook bellcrank and a long pushrod responsive to a left handle lever;
an arm rocker bellcrank, a bearing ball, a pivot rocker bellcrank, and end pushrod responsive to the long pushrod; and
a shoulder paddle, a shoulder cam assembly, a shoulder cam follower and a shoulder cam pin responsive to the end pushrod for locking and unlocking the shoulder joint.

38. The device of claim 34 wherein components of the wrist joint reside in a bore of a wrist ring and comprise a center disk, an axially inner pair of thrust washers bordering the center disk, a pair of thrust bearings bordering the inner pair of thrust washers, an axially outer pair of thrust washers bordering the thrust bearings and a pair of center halves bordering the axially outer thrust washers, the center halves and wrist ring being rotationally fixed relative to each other in the locked state of the wrist joint and rotatable about a bore axis relative to each other in the unlocked state of the wrist joint.

39. The device of claim 34 wherein components of the elbow joint reside in a bore of an elbow ring and comprises an arm, pivot, the arm pivot and elbow ring being rotationally fixed relative to each other in the locked state of the elbow joint and rotatable about a bore axis relative to each other in the unlocked state of the elbow joint.

40. The device of claim 34 wherein components of the shoulder joint reside in a bore of a shoulder ring and include a pivot assembly comprising a two piece ball pivot and a ball pivot shaft secured to the ball pivot, the pivot assembly and the shoulder ring being rotationally fixed relative to each other in the locked state of the shoulder joint and rotatable about a bore axis relative to each other in the unlocked state of the shoulder joint.

41. A device for supporting and positioning a part of a patient's body, comprising:
at least two joints each having a locked state and an unlocked state;
a release system for allowing an operator to select between the locked state and the unlocked state, the release system having an operator interface remote from the joints and at a location that enables the operator to support the weight of the body part while at least one of the joints is in the unlocked state,
wherein deformable rings circumscribe components of each of the joints, the operator interface includes a left operator interface and a right operator interface, the left and right operator interfaces arranged such that each motion transfer system can operate all the deformable rings to lock and unlock all the joints independently of the other motion transfer system.

42. A device for supporting and positioning a part of a patient's body, comprising:
at least two joints each having a locked state and an unlocked state;
a release system for allowing an operator to select between the locked state and the unlocked state, the release system having an operator interface remote from the joints and at a location that enables the operator to support the weight of the body part while at least one of the joints is in the unlocked state, and a mount selectively slidably engaged with a shoulder joint, the mount including a frame mount and a frame latch for securing the mount to a host device wherein the host device is an operating table.

43. The device of claim 42 wherein the mount spans between a pair of rectangular cross sectional rails of the host device.

44. The device of claim 43 wherein the rectangular cross sectional rails are carbon fiber rails.

* * * * *